(12) United States Patent
Allam et al.

(10) Patent No.: US 12,239,741 B1
(45) Date of Patent: *Mar. 4, 2025

(54) HYDROXYAPATITE-ENCLOSED ZINC PHOSPHATE NANOCOMPOSITE

(71) Applicant: IMAM MOHAMMAD IBN SAUD ISLAMIC UNIVERSITY, Riyadh (SA)

(72) Inventors: Ahmed A Allam, Riyadh (SA); Hassan A. Rudayni, Riyadh (SA); Mostafa R. Abukhadra, Riyadh (SA); Islam R. Sayed, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/915,867

(22) Filed: Oct. 15, 2024

Related U.S. Application Data

(63) Continuation of application No. 18/640,787, filed on Apr. 19, 2024, now Pat. No. 12,151,027.

(51) Int. Cl.
*A61K 9/20* (2006.01)
*A61K 31/555* (2006.01)
*B82Y 5/00* (2011.01)

(52) U.S. Cl.
CPC .......... *A61K 9/2072* (2013.01); *A61K 9/2009* (2013.01); *A61K 9/205* (2013.01); *A61K 31/555* (2013.01); *B82Y 5/00* (2013.01)

(58) Field of Classification Search
CPC ..... A61K 31/555; A61K 9/205; A61K 9/2009
See application file for complete search history.

(56) References Cited

U.S. PATENT DOCUMENTS

| | | | |
|---|---|---|---|
| 2002/0028243 | A1 | 3/2002 | Masters |
| 2005/0227910 | A1 | 10/2005 | Yang et al. |
| 2013/0039981 | A1 | 2/2013 | Cherurkuri |

FOREIGN PATENT DOCUMENTS

| | | |
|---|---|---|
| CN | 103751851 A | 4/2014 |
| CN | 111840572 A | 10/2020 |

OTHER PUBLICATIONS

Okasha et al. ; Synthesis and characterization of Mg-hydroxypatite and its cellulose hybridized structure as enhanced bio-carrier of oxaliplatin drug; equilibrium and release kinetics ; RSC Advances 13 ; Sep. 28, 2023 ; 17 Pages.
Sayed et al., "Synthesis and characterization of chitosan hybridized zinc phosphate/ hydroxyapatite core shell nanostructure and its potentiality as delivery system of oxaliplatin drug", vol. 254, Part 1, Oct. 2023, 127734 (Year: 2023).

*Primary Examiner* — James W Rogers
(74) *Attorney, Agent, or Firm* — Oblon, McClelland, Maier & Neustadt, L.L.P.

(57) ABSTRACT

A drug delivery system including a nanocomposite. The nanocomposite includes a zinc phosphate core, a hydroxyapatite shell, and chitosan. The hydroxyapatite shell at least partially encloses the zinc phosphate core. Further, the chitosan at least partially wraps around the hydroxyapatite shell. The chitosan interacts with the hydroxyapatite shell through hydrogen bonding, and the nanocomposite is loaded with oxaliplatin to form the drug delivery system.

20 Claims, 25 Drawing Sheets

HYDROXYAPATITE-ENCLOSED ZINC PHOSPHATE NANOCOMPOSITE

CROSS-REFERENCE TO RELATED APPLICATIONS

The present application is a Continuation of U.S. application Ser. No. 18/640,787, now allowed, having a filing date of Apr. 19, 2024.

STATEMENT OF PRIOR DISCLOSURE BY INVENTOR

Aspects of the present disclosure are described in I. R. Sayed, H. E. Alfassam, M. I. El-Sayed, I. M. Abd El-Gaied, A. A. Allam, and M. R. Abukhadra, "Synthesis and characterization of chitosan hybridized zinc phosphate/hydroxyapatite core shell nanostructure and its potentiality as delivery system of oxaliplatin drug"; International Journal of Biological Macromolecules; 2023; 254; 127734, incorporated herein by reference in its entirety.

STATEMENT OF ACKNOWLEDGEMENT

Support provided by the Princess Nourah bint Abdulrahman University Researchers Supporting Project number (PNURSP2023R400), Princess Nourah bint Abdulrahman University, Riyadh, Saudi Arabia, is gratefully acknowledged.

BACKGROUND

Technical Field

The present disclosure is directed to a drug delivery system, particularly a chitosan hybridized zinc phosphate/hydroxyapatite nanostructure-based drug delivery system for anticancer agents.

Description of Related Art

The "background" description provided herein presents the context of the disclosure generally. The work of the presently named inventors, to the extent it is described in this background section, as well as aspects of the description that may not otherwise qualify as prior art at the time of filing, are neither expressly nor impliedly admitted as prior art against the present invention.

About 72% of deaths worldwide are due to non-contagious illnesses, primarily cancer, with the percentage expected to rise to 75% in the future. Colorectal cancer, a common malignant form, affects around 13% of people and is one of the main factors inducing death and increasing the global mortality rate. Chemotherapy drugs are often used to combat the proliferation of cancerous cells, but many have toxic impacts on healthy cells and serious adverse effects, particularly when given at high dosages.

Traditionally, chemotherapy for cancer cells that have metastasized to other areas of the body has involved the use of the medication oxaliplatin (OXPN). The reason for the usage of the OXPN is its ability to create reactive platinum-based chemical compounds that prevent cancer cells from proliferating through deoxyribonucleic acid (DNA) replication. Additionally, its intracellular metabolites can create covalent bonds with DNA double strands, which inhibit the replication and transcription of cancer cells' DNA. However, the OXPN biochemical structure exhibits substantial poor solubility properties in the human bloodstream and considerable pernicious aspects of its determined metabolite qualities in healthy tissues. Additionally, digestive issues, GI problems, nausea, neurotoxicity, cardiac toxicity, mouth soreness, and myelotoxicity have all been listed as significant adverse impacts of OXPN. As a result, numerous enhanced delivery strategies have been investigated as successful methods for increasing the therapeutic effectiveness, selectivity, and solubility of OXPN.

Research has explored various biomaterials, including mesoporous silica, lipid nanoparticles, polymers, liposomes, alginate nanogels, bentonite/cellulose composites, and hydroxyapatite (HAP), as potential carriers of chemotherapeutic drugs. HAP, a valuable biomaterial, is widely used in medical sectors due to its chemical stability, surface area, and ion exchange capacity. However, the hydrophilic properties of HAP reduce its efficiency as a carrier of common drugs. Studies have focused on the shape, chemical composition, crystallite size, surface functionalization, and hybridization with polymers to improve HAP's properties.

Another biopolymer with a role in various pharmaceutical, environmental, and medical applications, particularly as a drug carrier, is chitosan. Chitosan is a polyaminosaccharide polymer that has technical benefits and is easy to make from the chitin part of different biogenic sources. Chitosan chains have safety, hemostatic ability, bioactivity, antimicrobial capacity, biocompatibility, and biodegradability in addition to high mechanical and adsorption properties.

Despite several biopolymers being investigated as anticancer drug delivery agents, there still exists a need for an improved drug delivery system. Therefore, there is an unmet requirement for a low-cost and effective delivery system for the administration of anticancer medicines. It is an object of the present disclosure to provide a drug delivery system which overcomes the limitation of the prior art.

SUMMARY

In an exemplary embodiment, a drug delivery system is described. The drug delivery system includes a nanocomposite. The nanocomposite includes a zinc phosphate core, a hydroxyapatite shell, and a chitosan. The hydroxyapatite shell at least partially encloses the zinc phosphate core. Further, the chitosan at least partially wraps around the hydroxyapatite shell. The chitosan interacts with the hydroxyapatite shell through hydrogen bonding, and the nanocomposite is loaded with an oxaliplatin to form the drug delivery system.

In some embodiments, the hydroxyapatite shell is in a form of nanorods.

In some embodiments, the nanorods have an average length of 1-10 micrometers ($\mu$m).

In some embodiments, the nanorods have an average width of 5-400 nanometers (nm).

In some embodiments, the crystallite size of a hydroxyapatite within the hydroxyapatite shell is 6-8 nm.

In some embodiments, the crystallite size of a zinc phosphate in the zinc phosphate core is 7-9 nm.

In some embodiments, the zinc phosphate core and the hydroxyapatite shell are separate crystalline phases.

In some embodiments, the zinc phosphate core is porous and includes nanopores and micropores.

In some embodiments, the zinc phosphate core is spherical and has an average diameter of 10-100 $\mu$m.

In some embodiments, the nanocomposite has a BET surface area of 120-140 square meters per gram ($m^2/g$).

In some embodiments, the nanocomposite has an average pore diameter of 25-35 nm.

In some embodiments, the nanocomposite comprises oxygen (O), nitrogen (N), phosphorus (P), calcium (Ca), magnesium (Mg), and zinc (Zn).

In some embodiments, 300-350 milligrams (mg) of oxaliplatin are included in the drug delivery system per gram of the nanocomposite when loading conditions are maintained at 20-30 degrees centigrade (° C.), pH 6-8, and for a minimum of 6 hours.

In some embodiments, the oxaliplatin interacts with the hydroxyapatite shell and the chitosan through at least one of van der Waals forces, hydrogen bonding, electrostatic interactions, chemical complexes, and ion exchange.

In some embodiments, a portion of the oxaliplatin is entrapped in the pores of the nanocomposite.

In some embodiments, the oxaliplatin, the zinc phosphate core, the hydroxyapatite shell, and the chitosan do not interact through covalent bonds.

In some embodiments, the release percentage of the oxaliplatin is at least 50% after 22 hours in an environment having a pH 7.4.

In some embodiments, the release percentage of the oxaliplatin is 100% after 140 hours in an environment having a pH of 7.4.

The foregoing general description of the illustrative present disclosure and the following The detailed descriptions thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
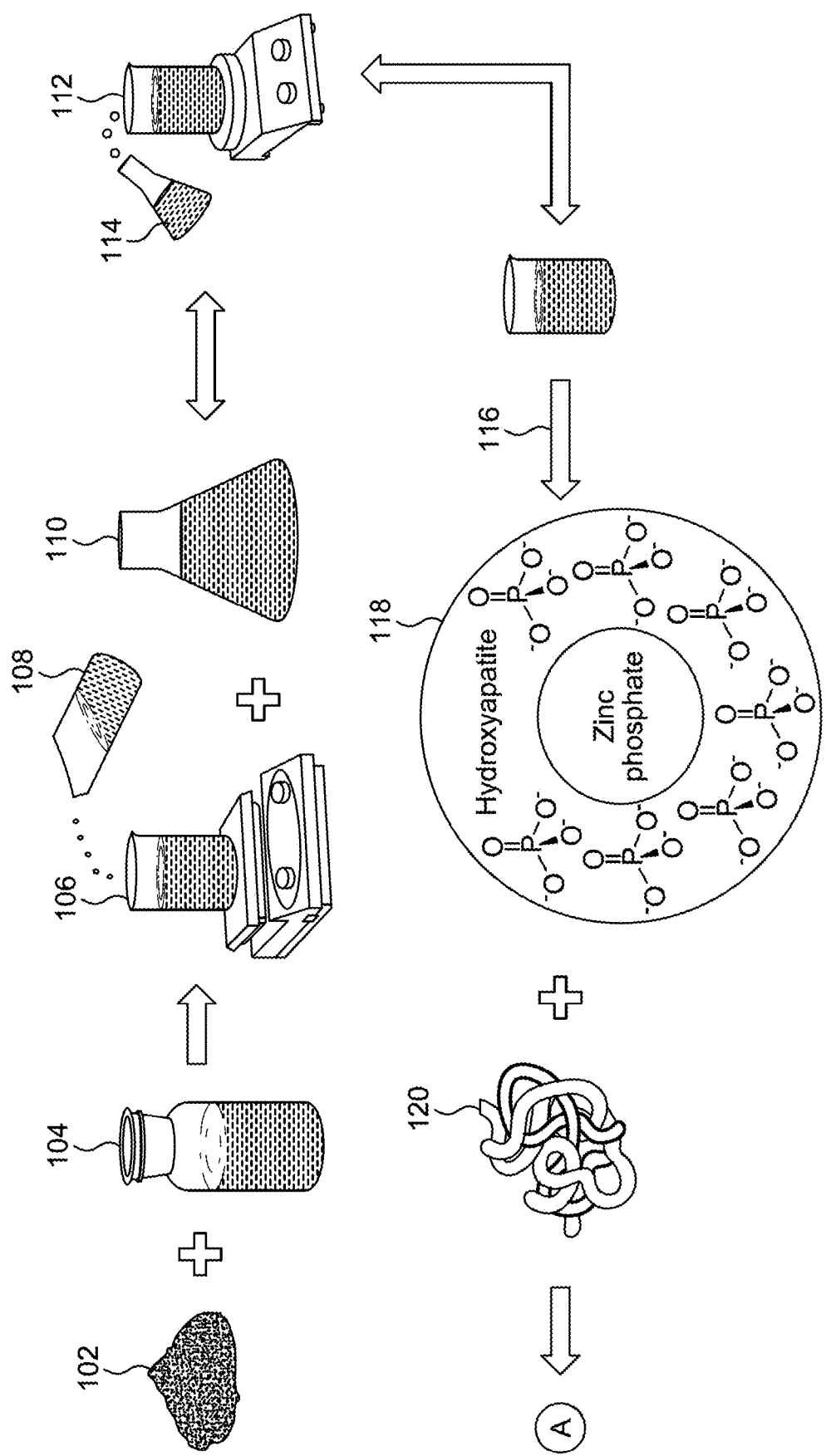
FIG. 1 illustrates a schematic diagram for the synthesis of a zinc phosphate/hydroxyapatite nanorod core-shell (ZPh/HPA$_{NRs}$) and a chitosan@zinc phosphate/hydroxyapatite nanorod core-shell composite (CH@ZPh/HPA$_{NRs}$) composite, according to certain embodiments.
Figure 1:
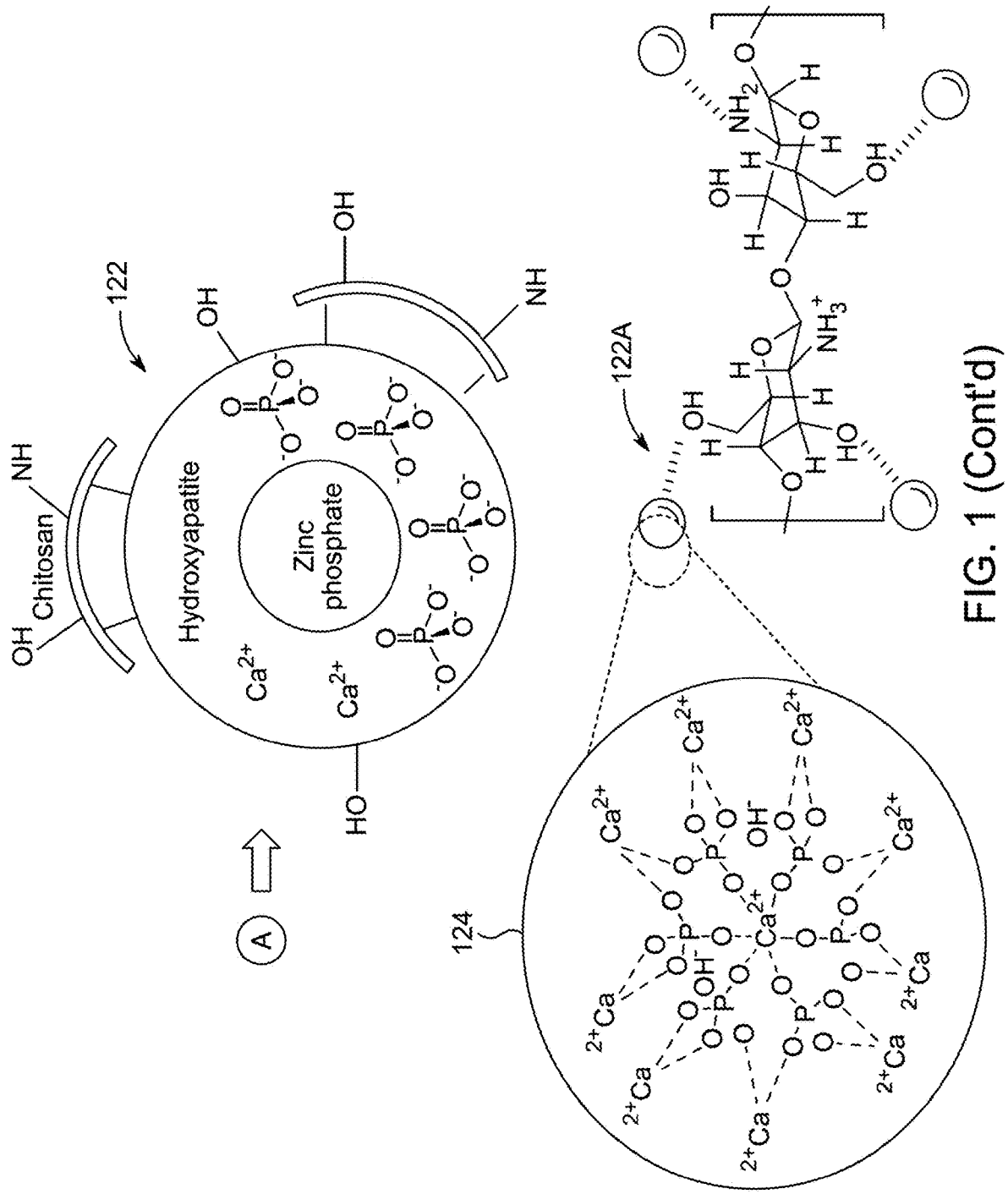

In the drawings, reference numerals designate identical or corresponding parts throughout the several views. Further, as used herein, the words "a," "an" and the like generally carry a meaning of "one or more," unless stated otherwise.

Where a numerical limit or range is stated herein, the endpoints are included. Also, all values and subranges within a numerical limit or range are specifically included as if explicitly written out.

Furthermore, the terms "approximately," "approximate," "about," and similar terms generally refer to ranges that include the identified value within a margin of 20%, 10%, or preferably 5%, and any values therebetween.

As used herein, the term "nanoparticle" refers to a particle wherein the longest diameter is less than or equal to 1000 nanometers.

As used herein, the term "nanocomposite" refers to a multiphase material in which, in contrast to micro composites, one of the phases has one, two, or three dimensions of less than 100 nm, or the composite phases have nanoscale distances between them.

As used herein, the term "nanorods" refers to one of the many structures that can be formed at the nanoscale. They are elongated nanoparticles with a rod-like shape.

As used herein, the term "anti-cancer agent" refers to a molecule (e.g., compound, peptide, protein, nucleic acid) used to treat cancer by destroying or inhibiting cancer cells or tissues. Anticancer agents may be selective for certain cancers or certain tissues. In embodiments, anticancer agents herein may include epigenetic inhibitors and multi-kinase inhibitors.

Aspects of the present disclosure are directed towards a zinc phosphate/hydroxyapatite core-shell nanocomposite (ZPh/HPA$_{NRs}$) and a chitosan hybridized zinc phosphate/hydroxyapatite core-shell nanocomposite (CH@ZPh/HPA$_{NRs}$) with enhanced anticancer properties that improve the delivery structure of traditional chemotherapy drugs during the treatment of colorectal cancer cells. The nanocomposite of the present disclosure is can deliver an anticancer agent, e.g., an oxaliplatin drug (OXPN), to the target tissue. These OXPN drug delivered by the composite of the present disclosure overcomes drawbacks such as poor solubility, digestive issues, nausea, neurotoxicity, cardiac toxicity, and other pernicious aspects in healthy tissues, thus, solving the limitations faced by the current technology present in the market.

A drug delivery system is described. The system includes a nanocomposite. The nanocomposite includes a core and a shell surrounding the core. The core includes zinc phosphate particles (also referred to as a zinc phosphate core), and the shell includes hydroxyapatite (also referred to as a hydroxyapatite shell).

In some embodiments, the zinc phosphate core is in a form of a microparticle having an average size of 10-100 micrometers (μm), preferably 20-90 μm, 30-80 μm, 40-70 μm, or 50-60 μm. The microparticle zinc phosphate core may exist in various morphological shapes, such as spheres, wires, crystals, sheets, rectangles, triangles, pentagons, hexagons, prisms, disks, cubes, ribbons, blocks, beads, toroids, discs, barrels, granules, whiskers, flakes, foils, powders, boxes, stars, tetrapods, belts, urchins, flowers, etc., and mixtures thereof. In a preferred embodiment, the microparticle zinc phosphate core has a spherical shape. In some embodiments, the zinc phosphate in the zinc phosphate core has an average crystallite size of 7-9 nm, preferably 7.2-8.8 nm, 7.4-8.6 nm, 7.6-8.4 nm, 7.8-8.2 nm, or about 8.0 nm.

In some embodiments, the zinc phosphate core is porous and includes nanopores and/or micropores. The term nanopore is used throughout to describe a pore having a longest dimension of 1-100 nm preferably 10-90 nm, 20-80 nm, 30-70 nm, 40-60 nm or about 50 nm. The term micropore is used throughout to describe a pore having a longest dimension of greater than 500 nm, preferably 0.5-10 μm, preferably 1-9 μm, 2-8 μm, 3-7 μm, 4-6 μm, or about 5 μm.

The shell is a hydroxyapatite shell that at least partially encloses the zinc phosphate core. Hydroxyapatite is a naturally occurring mineral form of calcium apatite with the formula $Ca_5(PO_4)_3(OH)$, often written $Ca_{10}(PO_4)_6(OH)_2$ to denote that the crystal unit cell comprises two entities. In some embodiments, during the synthesis of the nanocomposite a portion of the Ca in the hydroxyapatite is replaced with Zn from the zinc phosphate, preferably less than 30%, 20%, 10%, 5%, or 1% of the Ca atoms are replaced, relative to a total number of Ca atoms in the hydroxyapatite.

In some embodiments, the shell encloses at least 50% of the core, preferably 60%, 70%, 80%, 90%, or 100%. Encloses is defined as being present on a surface of and surrounding the core. In some embodiments, the hydroxyapatite shell completely encapsulates the core.

The hydroxyapatite shell may exist in various morphological shapes, such as nanospheres, nanowires, nanocrystals, nanosheets, nanorectangles, nanotriangles, nanopentagons, nanohexagons, nanoprisms, nanodisks, nanocubes, nanoribbons, nanoblocks, nanobeads, nanotoroids, nanodiscs, nanobarrels, nanogranules, nanowhiskers, nanoflakes, nanofoils, nanopowders, nanoboxes, nanostars, tetrapods, nanobelts, nano-urchins, nanoflowers, etc., and mixtures thereof. In a preferred embodiment, the hydroxyapatite shell is in a form of nanorods.

In some embodiments, the nanorods have an average length of 1-10 μm, preferably 2-9 μm, 3-8 μm, 4-7 μm, or about 5-6 μm. In some embodiments, the nanorods have an average width of 5-400 nm, preferably 50-350 nm, 100-300 nm, 150-250 nm, or about 200 nm. In some embodiments, the crystallite size of a hydroxyapatite within the hydroxyapatite shell is 6-8 nm, preferably 6.2-7.8 nm, 6.4-7.6 nm, 6.6-7.4 nm, 6.8-7.2 nm, or about 7.0 nm.

In some embodiments, the nanorods are randomly oriented. In some embodiments, the nanorods run parallel to each other. In a preferred embodiment, the nanorods run tangentially to the surface of the zinc phosphate core. In some embodiments, the random intersection between the nanorods results in a nanoporous matrix.

In some embodiments, the zinc phosphate core and the hydroxyapatite shell are separate crystalline phases, e.g., the zinc phosphate core and the hydroxyapatite shell do not interpenetrate. In other words, the zinc phosphate core and the hydroxyapatite shell do not interact through covalent bonds and do not affect the others' crystal structure. Instead, the zinc phosphate core and the hydroxyapatite shell interact through electrostatic interactions.

The nanocomposite further includes chitosan that at least partially wraps around the hydroxyapatite shell. In some embodiments, the chitosan wraps around at least 50% of the shell, preferably 60%, 70%, 80%, 90%, or 100%. The chitosan interacts with the hydroxyapatite shell through hydrogen bonding, preferably only hydrogen bonding. In some embodiments, the chitosan has a weight average molecular weight of 10,000-200,000 kDa, preferably 20,000-180,000 kDa, 40,000-160,000 kDa, 60,000-140,000 kDa, 80,000-120,000 kDa, or about 100,000 kDa.

In some embodiments, the nanocomposite includes the zinc phosphate core, the hydroxyapatite shell, and the chitosan. In some embodiments, the nanocomposite has a BET surface area of 120-140 $m^2/g$, preferably 125-135 $m^2/g$, or about 130 $m^2/g$. In some embodiments, the nanocomposite has a BET surface area of 100-500 $m^2/g$, preferably 150-450 $m^2/g$, 200-400 $m^2/g$ or about 250-350 $m^2/g$. In some embodiments, the nanocomposite has an average pore diameter of 25-35 nm, preferably 27-33 nm, or 29-31 nm. The nanocomposite includes oxygen (O), nitrogen (N), phosphorus (P), calcium (Ca), magnesium (Mg), and zinc (Zn), preferably these are the only elements present in the nanocomposite.

In some embodiments, the nanocomposite includes 30-80 wt. %, preferably 35-75 wt. %, 40-70 wt. %, 45-65 wt. %, or 50-60 wt. % of the zinc phosphate core, 10-40 wt. %, preferably 15-35 wt. %, or 20-30 wt. % of the hydroxyapatite shell, and 5-30 wt. %, preferably 10-25 wt. %, or preferably 15-20 wt. % of the chitosan, based on a total weight of the nanocomposite.

The drug delivery system of the present disclosure is adapted to deliver a drug to an organ or tissue of interest. In an embodiment, the drug is a chemotherapeutic or anticancer drug. In an embodiment, the anticancer agent may include alkylating agents such as cyclophosphamide, platins, and temozolomide; antimetabolites such as methotrexate and 5-fluorouracil; topoisomerase inhibitors such as etoposide and irinotecan; and mitotic inhibitors such as paclitaxel and vincristine. In a preferred embodiment, chemotherapy agents are used that include metal platinum complexes also known as platinum drugs. In some embodiments, types of platinum drugs include cisplatin, carboplatin, lobaplatin, and satraplatin. In some embodiments, platin drugs are used in combination with other chemotherapy drugs. In a preferred embodiment, oxaliplatin is used.

In some embodiments, the oxaliplatin interacts with the zinc phosphate core, the hydroxyapatite shell and the chitosan through at least one of van der Waals forces, hydrogen bonding, electrostatic interactions, chemical complexes, and ion exchange, preferably through more than one interactive force. The oxaliplatin is preferably not bound to the zinc phosphate core, the hydroxyapatite shell, and the chitosan via a covalent bond. In some embodiments, the oxaliplatin, the zinc phosphate core, the hydroxyapatite shell, and the chitosan do not interact through covalent bonds. In other words, each component is a separate entity that interacts with the others through electrostatic and molecular forces. In some embodiments, a portion of the oxaliplatin is entrapped in the pores of the nanocomposite, preferably 10%, 20%, 30%, 40%, 50%, 60%, 70%, 80%, 90%, or 95% by weight of the oxaliplatin is entrapped in the pores. The pores of the nanocomposite may be the pores of the hydroxyapatite shell and/or the pores of the zinc phosphate core.

In some embodiments, the loading of the oxaliplatin occurs by mixing solutions of the oxaliplatin with the nanocomposite under specific conditions. In some embodiments, the oxaliplatin is loaded onto the nanocomposite at a pH of 3-8, preferably 4-7, or 5-6. In some embodiments, the oxaliplatin is more soluble at low pH, which negatively impairs the loading qualities, therefore preferably the pH is 6-8. In some embodiments, the loading occurs for 1-15 hours, preferably 2-14 hours, 3-13 hours, 4-12 hours, 5-11 hours, 6-10 hours, or 7-9 hours. In some embodiments, the loading occurs at a temperature of 20-60° C., preferably 30-50° C., or about 40° C. In some embodiments, 300-350 milligrams (mg) of oxaliplatin, preferably 310-340 mg, or 320-330 mg are included in the drug delivery system per gram of the nanocomposite when loading conditions are maintained at 20-30 degrees centigrade (° C.), pH 6-8, and for a minimum of 6 hours. In some embodiments, the nanocomposite has a higher loading capacity of the oxaliplatin than a same nanocomposite but without the chitosan. In some embodiments, the nanocomposite can load 5-15 oxaliplatin molecules per site, preferably 6-14, 7-13, 8-12, 9-11 or about 10.

In some embodiments, a release percentage of the oxaliplatin from the drug delivery system is greater than 10%, preferably greater than 20%, preferably greater than 30%, preferably greater than 40%, preferably at least 50% by weight based on the total amount of the oxaliplatin in the drug delivery system prior to release after 22 hours in an environment having a pH of 7.4. In some embodiments, a release percentage of the oxaliplatin from the drug delivery system includes greater than 50%, preferably greater than 60%, preferably greater than 70%, preferably greater than 80%, preferably at least 100% after 140 hours in an environment having a pH of 7.4.

While not wishing to be bound to a single theory, it is thought that the high loading capacity of the nanocomposite is due to incorporation of the chitosan which (1) increased surface area (2) increased the organophilic properties of the composite displaying enhanced affinities for the organic molecules and (3) resulted in substantial rise in the total number of active sites owing to the integration of extra active chemical groups. Also, the chitosan improved the release properties of the nanocomposite because the chitosan chains create barriers that exist between the medication and the reactive sites of the hydroxyapatite, reducing the total number of formed complexes and entrapped ions.

In some embodiments, the nanocomposite loaded with oxaliplatin has a higher toxicity towards cancer cells than towards healthy cells. In some embodiments, the nanocomposite loaded with oxaliplatin has an $IC_{50}$ for colon cancer cells of 1-10 µg/mL, preferably 2-9 µg/mL, 3-8 µg/mL, 4-7 µg/mL, or 5-6 µg/mL. Half maximal inhibitory concentration ($IC_{50}$) is a measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%.

EXAMPLES

The following examples demonstrate the synthesis and characterization of chitosan hybridized zinc phosphate/hydroxyapatite core-shell nanostructure-based drug delivery system, as described herein. The examples are provided solely for illustration and are not to be construed as limitations of the present disclosure, as many variations thereof are possible without departing from the spirit and scope of the present disclosure.

Example 1: Materials

Chemicals Required

During the preparation stages of the apatite-based structure, natural Egyptian carbonate rocks were used as a source of calcium and magnesium. During the different stages of dissolving and making crystals, nitric acid ($HNO_3$, 40% purity; Sigma-Aldrich, Egypt), zinc chloride (>98.0% purity; Sigma-Aldrich, Egypt), phosphoric acid (88% purity; Sigma-Aldrich, Egypt), and $NH_4OH$ solution (25% $NH_3$, Sigma-Aldrich, Egypt) were used. The nanocomposite was made with analytical-grade acetic acid that was 99.8% pure and a de-acetylated chitosan biopolymer that had a molecular mass of 120,000 kDa. Both were bought from Sigma Aldrich in Egypt. Oxaliplatin ([SP-4-2-(1R-trans)]-(1,2-cyclohexane diamine-N, N') [ethanedioata(2-)-O, O] platinum) with a molecular weight of 397.29 was shipped from the Egyptian branch of the Sigma-Aldrich Company to be applied in the loading and release studies.

Cell Lines Required

Colorectal cancer cells (HCT-116; TACK, Rockville, MD), dimethyl sulfoxide (DMSO, 99%), (4-(2-hydroxyethyl)-1-piperazineethanesulfonic acid) (HEPES) buffer, RPMI-1640, Fetal Bovine Serum, 3(4,5-dimethylthiazol-2-yl)-2.5 bromide (MTT, 99%), trypsin-ethylenediaminetetraacetic acid (EDTA) (0.25%), and Dulbecco's Modified Eagle Medium (DMEM) were used to evaluate the in-vitro cytotoxicity effects of the free zinc phosphate/hydroxyapatite nanorod core-shell ($ZPh/HPA_{NRs}$) and chitosan@zinc phosphate/hydroxyapatite nanorod core-shell composite ($CH@ZPh/HPA_{NRs}$) as well as their oxaliplatin (OXPN) loading products.

Example 2: Synthesis of $ZPh/HPA_{NRs}$ Structure

FIG. 1 illustrates a schematic diagram for the synthesis of $ZPh/HPA_{NRs}$. The raw carbonate fraction was initially mechanically activated in a ball mill to a size range between 10 and 150 micrometers (m). The powdered fractions (35 grams (g)) (102) were gently dissolved into a solution (150 milliliters (mL)) of 40% nitric acid (104) at room temperature for 48 hours by a magnetic stirring device (500 revolutions per minute (rpm)) (106). Whatman filter paper (45 µm) was used to separate the solid residues from the filtrated solution, which is richer in the soluble $Ca^{2+}$ and $Mg^{2+}$ ions. The filtrated solution (150 mL) was subsequently mixed with the zinc chloride salt (10 g) (108), and the salt was dissolved completely over 5 hours of stirring. Following that, 150 mL of phosphoric acid 110, which is the primary precursor of the $PO_4^{3+}$ ions were added to the resulting mixture while it was continuously stirred for 2 hours (112). The hydroxyapatite product was subsequently produced using direct precipitation steps, which involved gently incorporating the ammonia solution (114) into the mixture while stirring and in the presence of ultrasonic radiation (240 watts (W)) for 60 mins. The solid fractions that had precipitated were rinsed with distilled water to be neutralized for 15 minutes and then transferred to the dryer (116), where they spent 24 hours at 100° C. $ZPh/HPA_{NRs}$ structure (118) is used in the subsequent characterization and the other experimental procedures.

Example 3: Synthesis of ($CH@ZPh/HPA_{NRs}$) Composite

Further, FIG. 1 also illustrates a schematic diagram for the synthesis of CH $@ZPh/HPA_{NRs}$ composite. Following the synthesis of the $ZPh/HPA_{NRs}$ structure (118), a homogeneous slurry of the product was initially produced by dispersing 2 g of its synthesized fractions within 50 mL of distilled water and sonicating the resulting mixture (at 240 W) for 120 min. 4 g of the powdered chitosan 120 was dissolved in 50 mL of the acetic acid (0.1%) as a separate test before being gently added to the $ZPh/HPA_{NRs}$ slurry. The mixture was stirred magnetically at 800 rpm for 24 hours while being subjected to 240 W of sonication vibrations. Following comprehensive washing, the resulting composite was filtered to remove any residual acid and dried in an oven at 60° C. overnight before being labelled as $CH@ZPh/HPA_{NRs}$ (122). When the interaction between $Ca^{2+}$ and $PO_4^{3+}$ is studied in a magnified image (124), the presence of hydrogen bond (122A) is observed.

Example 4: Characterization Techniques

An Empyrean PANalytical diffractometer was used to examine the X-ray diffraction (XRD) patterns of $ZPh/HPA_{NRs}$ and CH $@ZPh/HPA_{NRs}$. To investigate the crystalline nature and structural qualities of the materials, the rate of scanning was set to 5°/min, and the voltage at which it operated was calibrated to 40 kV. The Fourier-transform infrared spectroscopy (FT-IR) spectra were analyzed to evaluate the chemical changes. The spectra were obtained using a Fourier Transform Infrared spectrometer (FTIR-8400S; Shimadzu) with a frequency spectrum ranging from 400 to 4000 $cm^{-1}$. The morphological changes were investigated using images obtained from a Zeiss-Ultra 55 Gemini scanning electron microscope after coating the samples with a thin film of gold, and the acceleration voltage was evaluated with an experimental range from 5 up to 30 kV. The high-resolution transmission electron microscopy (HRTEM) images taken with a JEOLJEM2100 Transmission-Electron Microscope were used to investigate the interior structure and features at an acceleration voltage of 200 kV. The surface area analyzer Beckman Coulter SA3100 was used in the investigation to determine the distinctive surface area and distribution of pore sizes using the Brunauer-Emmett-Teller (BET) and Barrett, Joyner, and Halenda (BJH) methods, respectively.

Example 5: The Loading Properties of OXPN Studies

The loading properties of $ZPh/HPA_{NRs}$ and $CH@ZPh/HPA_{NRs}$ as potential carriers for OXPN were evaluated based on the effects of experimental loading conditions such as pH (between 3 and 8), loading interval (1 to 14 hours), concentration of drug (between 50 and 350 mg/L), and temperature (between 2° and 60° C.). Using a vortex rotator device, the $ZPh/HPA_{NRs}$ and $CH@ZPh/HPA_{NRs}$ particles were uniformly blended with the OXPN solutions. After the loading processes, Whatman filter paper was used to separate the drug containing $ZPh/HPA_{NRs}$ and $CH@ZPh/HPA_{NRs}$ particles from the OXPN solutions. An ultraviolet-visible (UV-Vis) spectrophotometer was used to measure the amounts of OXPN in the obtained filtrates at wavelengths of 209 nm. The loading capacities were calculated using Eq. (1), considering the determined drug concentrations in the filtrates. The loading experiments were carried out in triplicate, and all the computations and curves were displayed using the average values that resulted from those tests.

$$\text{Loaded drug (mg/g)} = \frac{(\text{Initial concentration} - \text{Residual concentration}) \times \text{solvent volume}}{\text{Carrier weight}} \quad (1)$$

Example 6: The In-Vitro Release Studies

The study examined the release characteristics of OXPN from ZPh/HPA$_{NRs}$ and CH@ZPh/HPA$_{NRs}$ particles under regulated circumstances while taking 37.5° C. as the release temperature. The acetate buffering solution (pH 5.5) and the saline solution with phosphate buffer (pH 7.4) were used to follow the release behavior of OXPN. For the release tests, predetermined amounts of ZPh/HPA$_{NRs}$ and CH@ZPh/HPA$_{NRs}$ particles holding OXPN (100 mg/g) were suspended individually in 500 mL of each of the various buffers and homogenized for a maximum duration of 150 hours via a DISTEK dissolution apparatus at a vessel revolving speed of 200 rpm. 5 mL of the buffering solutions were periodically taken out of the apparatus vessels during their mixing operation to measure the amounts of liberated OXPN. The UV-visible spectrophotometer was used to perform this at a maximum wavelength of 209 nm for the OXPN drug. To keep the buffer volume consistent throughout the in vitro diffusion periods, a 5 mL sample of the buffers was returned to the vessels that contained the bulk buffers after each drug measurement cycle. The releasing tests were run three times, and the average values from those three runs were used for both the computations and the graphing. The obtained OXPN concentrations were used to assess percentages of the released drug based on the calculation indicated by Eq. (2).

$$\text{Drug release \%} = \frac{\text{The amount of Released drug}}{\text{Amount of loaded drug}} \times 100 \quad (2)$$

Example 7: In-Vitro Cytotoxicity Studies

At first, HCT-116 cell lines were grown in an RPMI-1640 medium with 50 µg/mL gentamycin and 10% fetal calf serum. The cells were grown under specified humidity (5% $CO_2$) and temperature (37° C.) conditions. Three times each week, the HCT-116 cells were cultured before being suspended at a density of $5 \times 10^4$ cells per well in Corning®96-well plates and left to incubate for 24 hours. Following a 24-hour incubation period, specific amounts of free ZPh/HPA$_{NRs}$ and CH@ZPh/HPA$_{NRs}$, as well as their OXPN loading products, were administered to the culture plates as suspensions within 50 µL. The MTT test was used to measure the cellular viability and proliferation of the cancer cells under examination. Following a 48-hour incubation stage, the culture medium was replaced with freshly prepared RPMI-1640 media (100 µL) and consequently mixed with the MTT reagent (10 µL; 12 mM). After the last incubation time of 5 hours, the formazan that had been created was seen to have a purple hue and was ultimately dissolved with 50 µL of DMSO. A microplate reader operating at a wavelength of 590 nm was used to measure the optical density of the treated cells that were incubated. Next, using Eq. (3), the cell viability percentages were determined.

$$\text{Cell viability (\%)} = \frac{\text{Mean } OD}{\text{Control } OD} \times 100 \quad (3)$$

Example 8: Structural Characterization

Figure 2:
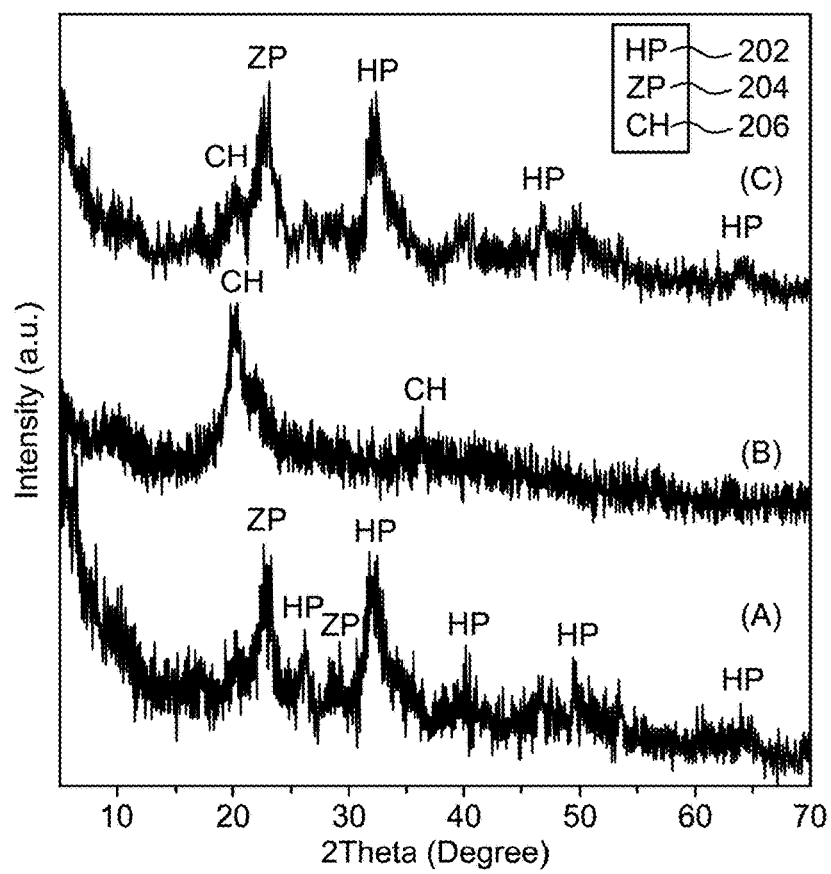
FIG. 2 illustrates X-ray diffraction (XRD) patterns of (A) ZPh/HPA$_{NRs}$ structure, (B) chitosan polymer, and (C) CH@ZPh/HPA$_{NRs}$, according to certain embodiments.

FIG. 2 shows the ZPh/HPA$_{NRs}$ (202), chitosan (204), and CH@ZPh/HPA$_{NRs}$ (206) structures acquired by X-ray diffraction (XRD) patterns. FIG. 2 (A) shows the observed pattern of ZPh/HPA$_{NRs}$ (202), hydrated hydroxyapatite (26.2°, 32.2°, 39.6°, and 48.5°) (Ref. Cd. 00-001-1008) was successfully formed in a composite with hydrated zinc phosphate (22.8°) (Ref. Cd. 00-010-0333). The hydroxyapatite and zinc phosphate phases were synthesized with estimated crystallite sizes of 7.4 nm and 8.5 nm, respectively. FIG. 2 (A) also shows the results of the XRD analysis revealing the formation of a hybrid structure consisting of two separate crystalline phases. This relates to the substitution of the functional ions of the early-produced apatite with extra $Zn^{2+}$ ions within the synthesis solutions.

FIG. 2 (B) shows the diffraction peaks at two angles of 10° and 22° in the pattern of the integrated polymer identifying the commercial chitosan polymer (204) with its semi-crystalline properties. FIG. 2 (C) illustrates the major peaks of the ZPh/HPA$_{NRs}$ framework are discernible in the CH@ZPh/HPA$_{NRs}$ (206) composite's XRD pattern but were slightly shifted to lower angles. Additionally, one of the two chitosan main peaks was not present, and the residual peak was relocated and merged with the peaks of apatite and phosphate to donate effective conjunction of both ZPh/HPA$_{NRs}$ (202) and chitosan biopolymer (204).

Figure 3:
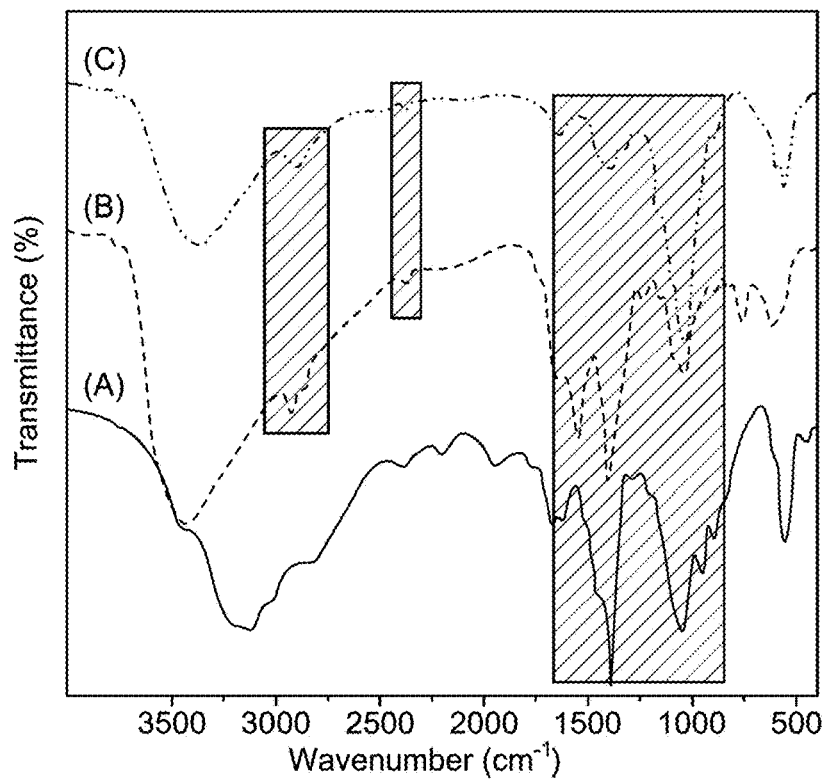
FIG. 3 illustrates Fourier-transform infrared spectroscopy (FT-IR) spectra of (A) ZPh/HPA$_{NRs}$ structure, (B) chitosan polymer, and (C) CH@ZPh/HPA$_{NRs}$, according to certain embodiments.

FIG. 3 illustrates FT-IR spectra of ZPh/HPA$_{NRs}$, chitosan, and CH@ZPh/HPA$_{NRs}$. FIG. 3 (A) illustrates the spectra of ZPh/HPA$_{NRs}$ showing the basic chemical groups of both apatite and zinc phosphate structures, such as $PO_4^{3+}$ (1041 and 556 cm$^{-1}$), $HPO_4^{2-}$ (954 and 896 cm$^{-1}$), Zn—O (454 cm$^{-1}$), H—OH (1666 and 1627 cm$^{-1}$) and O—H (3125 cm$^{-1}$). Additionally, a number of groups were recognized in the ZPh/HPA$_{NRs}$ spectrum, including the N—H ($NH_3^-$) group (1390 cm$^{-1}$) and $CO_3^{2-}$ group (1943 to 2376 cm$^{-1}$). The carbonate group was attributed to trapped $CO_2$ from the atmosphere or the dissolution of limestone during the preparation steps. During various stages of preparation, the N—H-containing groups were incorporated into the structure because of the use of nitric acid and ammonia.

FIG. 3 (B) illustrates N—H (1547 cm$^{-1}$), OH (3423 cm$^{-1}$), C—H (2925 and 1336 cm$^{-1}$), C═O (1637 cm$^{-1}$), C—O (1040 cm$^{-1}$), and C—N(1402 cm$^{-1}$) were the principal bands that were distinguished in the spectrum of chitosan, which was integrated in the formed CH@ZPh/HPA$_{NRs}$ composite. Following a successful integration process, FIG. 3 (C) illustrates the distinct CH@ZPh/HPA$_{NRs}$ spectrum shows notable changes either in the positions of the bands or their intensities, in addition to detection of complex bands that are related to both organic chitosan and inorganic apatite structure. The detectable chemical groups of chitosan are C—H (2906 cm$^{-1}$), C═O (1639 cm$^{-1}$), C—N(1404 cm$^{-1}$), and C—O (1061 cm$^{-1}$). FIG. 3 (C) also shows the identified groups of apatite and zinc phosphate are $PO_4^{3+}$ (1037 and 564 cm$^{-1}$), N—H group (1392 cm$^{-1}$), and $CO_3^{2-}$ group (2377 cm$^{-1}$). Such deviation in the positions of the FT-IR bands and declination in their determined intensities, in addition to the observable diminishing of the bands of some groups such as $HPO_4^{2-}$ in ZPh/HPA$_{NRs}$ and N—H in chitosan, validate the effective interaction between their active chemical groups during the formation of the composite.

Figure 4A:
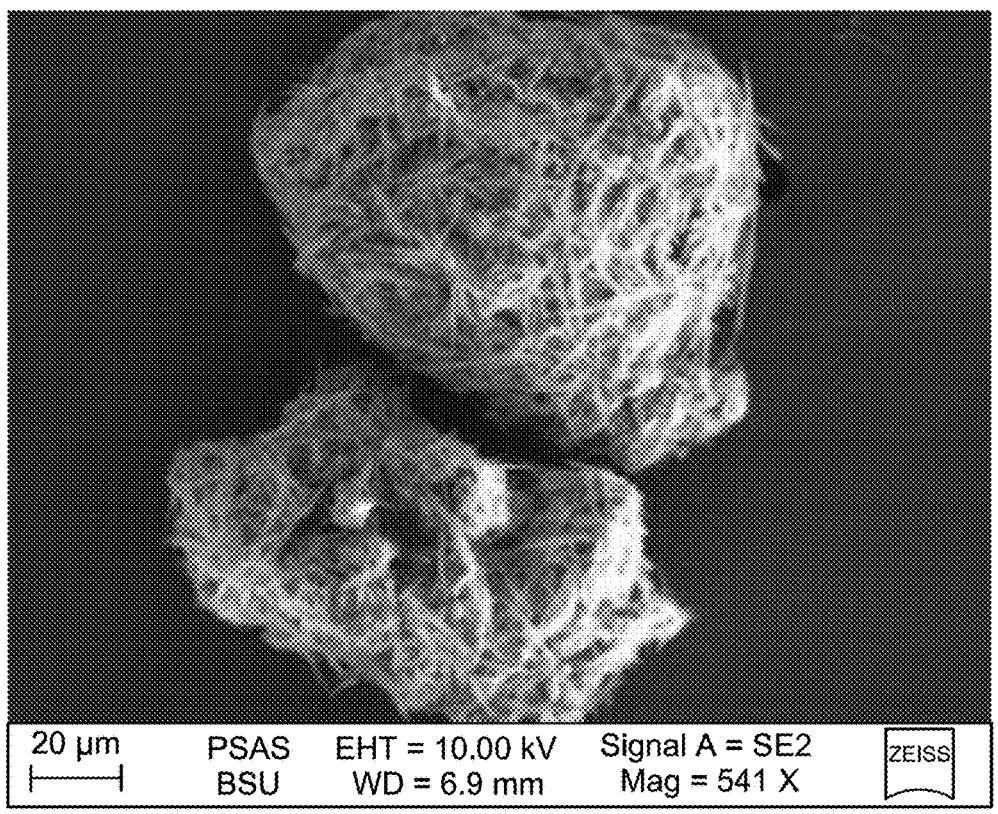
FIG. 4A illustrates a scanning electron microscope (SEM) image of ZPh/HPA$_{NRs}$ structure, according to certain embodiments.
Figure 4B:
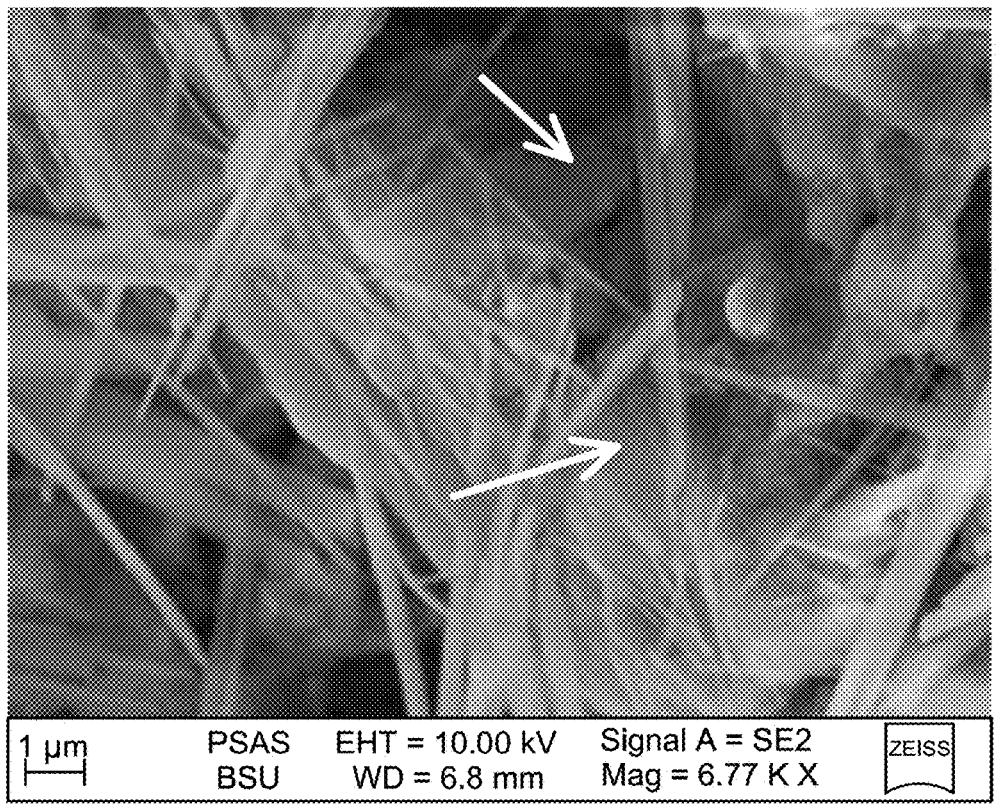
FIG. 4B illustrates the SEM image of a zinc phosphate substrate, according to certain embodiments.
Figure 4C:
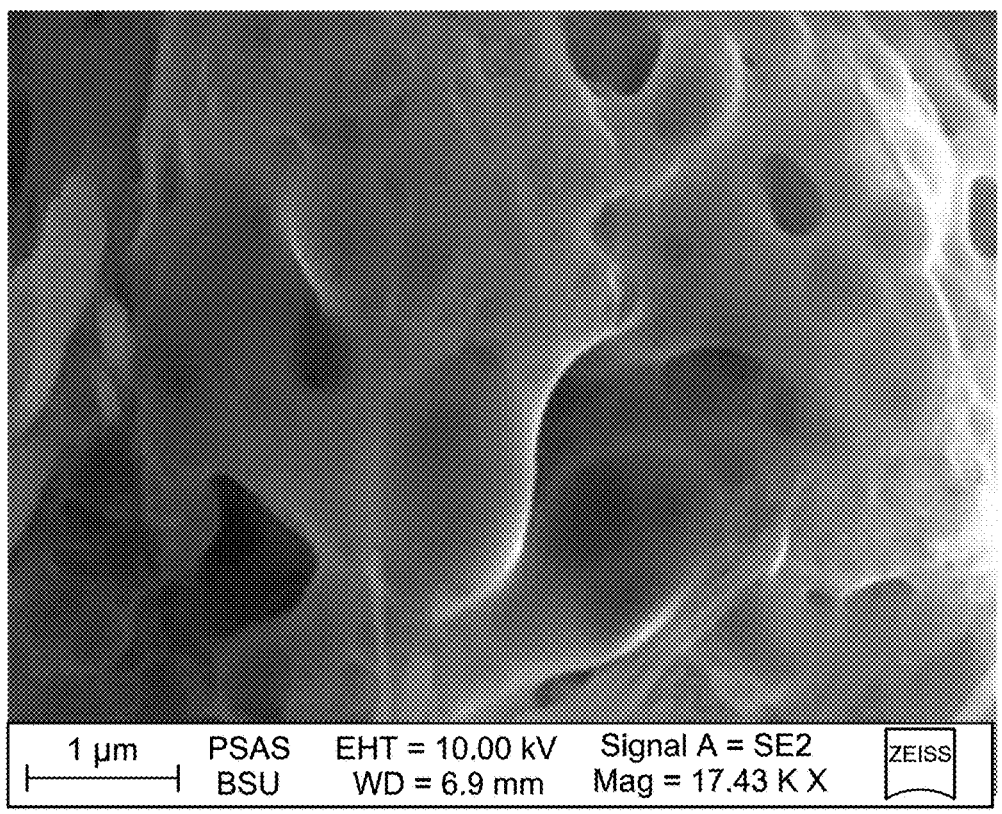
FIG. 4C is a SEM image showing porosity of zinc phosphate substrate, according to certain embodiments.

FIG. 4A illustrates the scanning electron microscope (SEM) images of the ZPh/HPA$_{NRs}$ demonstrating their hybrid nature and the existence of two components (hydroxyapatite and zinc phosphate) in the core-shell structure. FIG. 4B illustrates the SEM image of the zinc phosphate substrate. FIG. 4C illustrates the zinc phosphate component detecting as a massive, agglomerated, and porous substrate. The detected pores can be classified into two types, including structural nano-pores and micro-pores, as a result of the released gases during the preparation procedures.

Figure 4D:
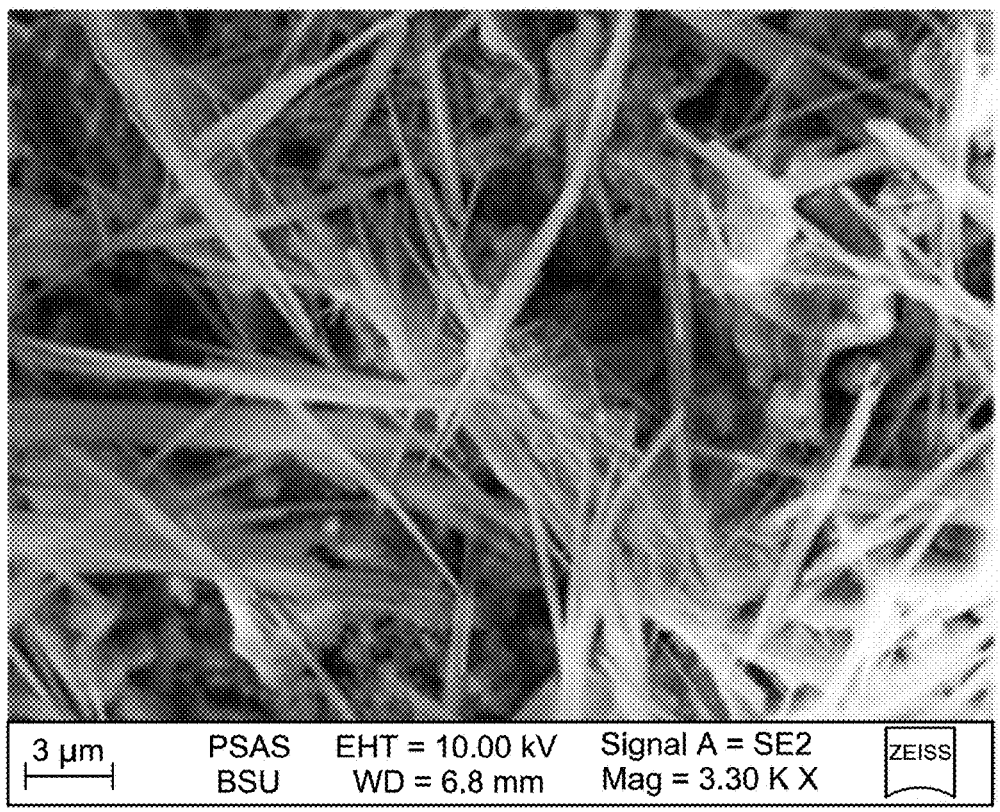
FIG. 4D is an SEM image depicting an intersection between the hydroxyapatite rods, according to certain embodiments.
Figure 4E:
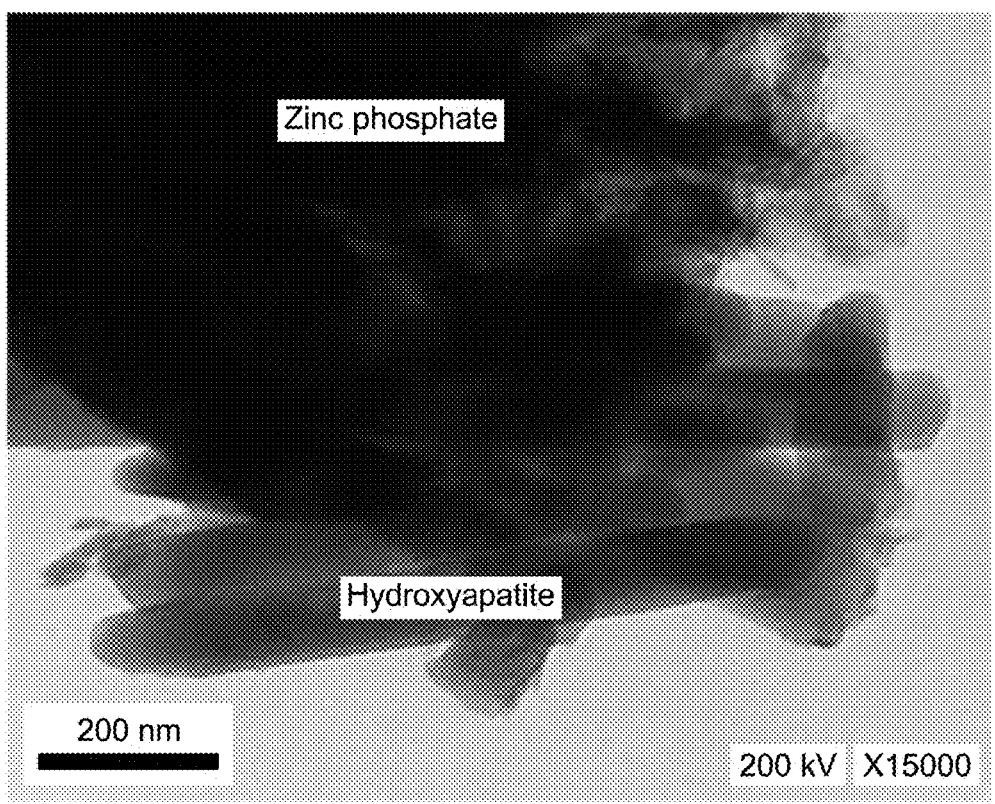
FIG. 4E illustrates a high-resolution transmission electron microscopy (HRTEM) image of the ZPh/HPA$_{NRs}$ structure, according to certain embodiments.
Figure 4F:
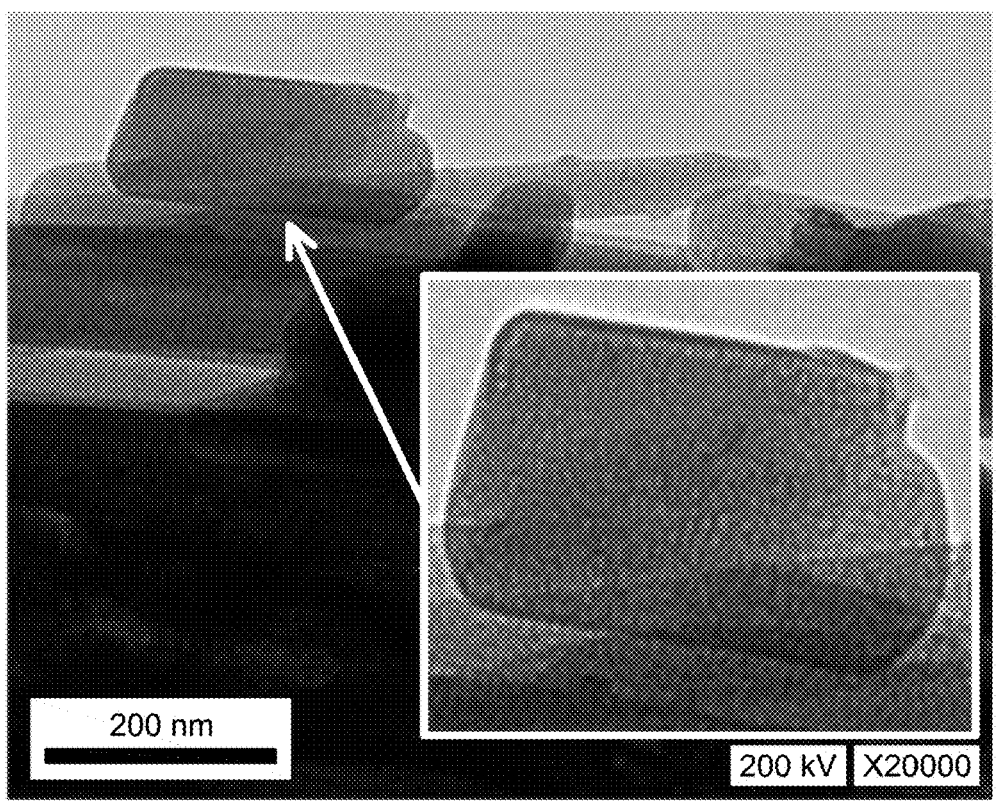
FIG. 4F is a HRTEM image showing the porous structure of hydroxyapatite rods, according to certain embodiments.

FIG. 4D illustrates the zinc phosphate substrate which is highly coated with hydroxyapatite grains that appear as notable nano-rods of well-developed morphology. The observed rods display an average diameter of 5 to 400 nm and an average length of 1 to 10 μm. The random intersection between these rods resulted in a notable nanoporous matrix. FIG. 4E shows the obtained high-resolution transmission electron microscopy (HRTEM) images agree with the detected features in the SEM images, showing the hydroxyapatite nanorods underlain by the zinc porous phosphate substrate. Moreover, FIG. 4F illustrates the high-magnification HRTEM image, revealing the highly porous nature of the hydroxyapatite nanorods.

Figure 4G:
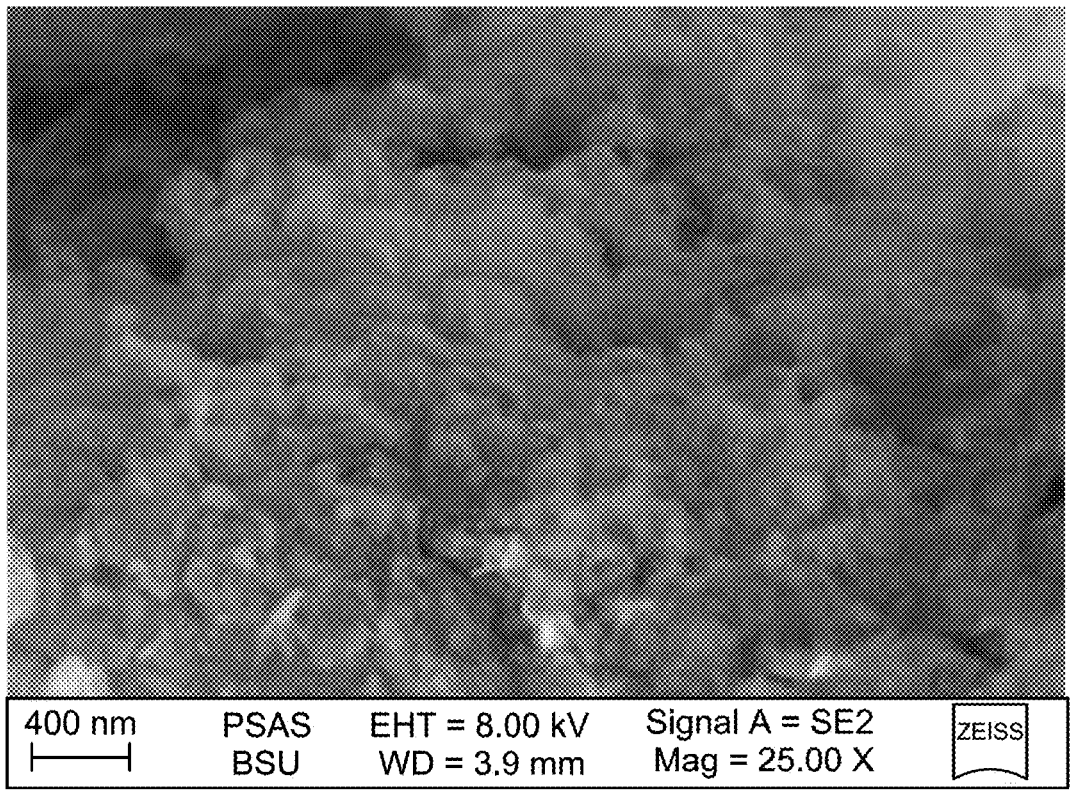
FIGS. 4G-4I illustrate SEM images of the CH@ZPh/HPA$_{NRs}$, according to certain embodiments.
Figure 4H:
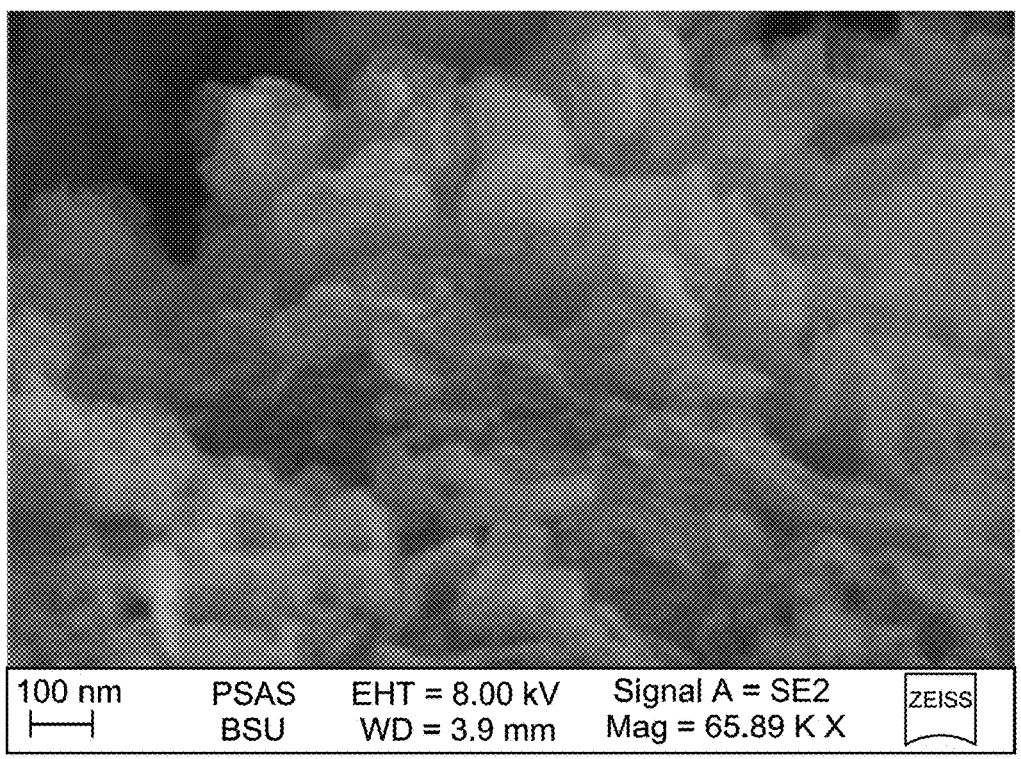
Figure 4I:

FIGS. 4G-4H illustrates the SEM images of the synthetic particles of the CH@ZPh/HPA$_{NRs}$ composite, demonstrating admixing between the ZPh/HPA$_{NRs}$ particles and the chitosan polymeric matrix, with reorientation and re-arrangement for the apatite grains. FIG. 4I illustrates the result in a rugged surface, and the admixed grains displayed various forms, including wormy, spherical, and crooked shapes. Such morphological changes are associated with notable changes in the textural properties, particularly the surface area and pore size distribution. The determined surface area, average pore diameter, and pore volume of the synthetic ZPh/HPA$_{NRs}$ are 138.2 m$^2$/g, 17.8 nm, and 0.572 cc/g, respectively. The formation of CH@ZPh/HPA$_{NRs}$ is associated with a slight increment in the surface area up to 133.4 m$^2$/g, which is related to the surficial topography of the composite. This is also accompanied by a reduction in the increase in the average pore diameter (28.6 nm) as a result of the interstitial micropores.

Figure 5A:
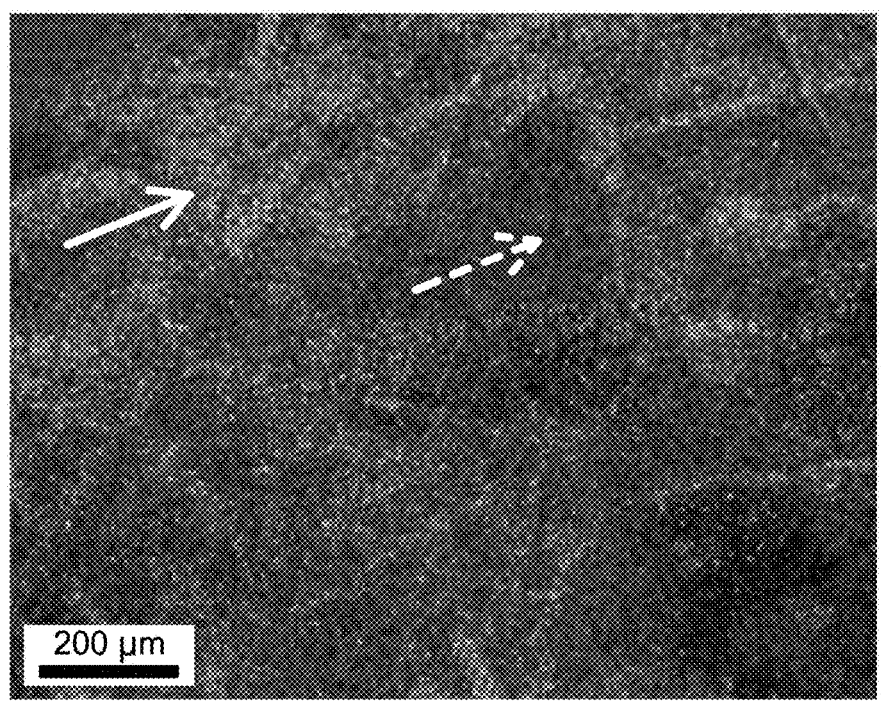
FIG. 5A illustrates a general energy-dispersive X-ray spectroscopy (EDX) map for the ZPh/HPA$_{NRs}$ structure declaring observable phase separation, according to certain embodiments.
Figure 5B:
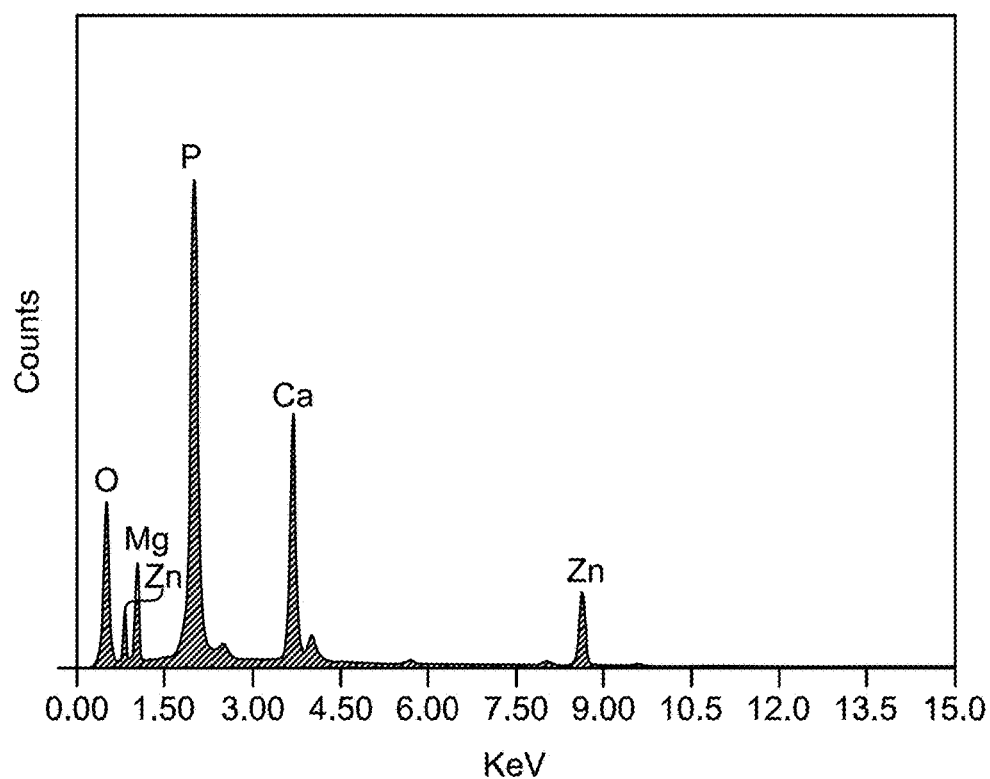
FIG. 5B illustrates a general EDX spectrum of ZPh/HPA$_{NRs}$ structure, according to certain embodiments.

FIG. 5A illustrates the general energy-dispersive X-ray (EDX) spectrum and map confirm the existence of the two phases with different chemical compositions. FIG. 5B illustrates the general EDX spectrum declaring the existence of oxygen (O), nitrogen (N), phosphorus (P), calcium (Ca), magnesium (Mg), and zinc (Zn) as the elements. The Ca$^{2+}$ and Mg$^{2+}$ ions are related to the used carbonate precursor, and the Zn ion is related to the used zinc solution. The spot EDX spectrum of the observed nanorods demonstrates the existence of O, P, Ca, and Mg as the elemental composition, which corresponds to the hydroxyapatite chemical structure. The spot inspection of the massive substrate demonstrates the presence of O, P, Ca, and Zn as its elemental composition, which corresponds to zinc phosphate phases that formed as later crystalline phases. Its formation is related to the formation of chemical complexes between the Zn$^{2+}$ ions in the synthesis solutions and the formed hydroxyapatite phase, or via ion exchange processes.

Example 9: Drug Loading Properties

Effect of pH: The experimental pH adaptation had an impact on the charge distributions on the surfaces of ZPh/HPA$_{NRs}$ and CH@ZPh/HPA$_{NRs}$, as well as the variation in speciation of OXPN. From pH 3 to pH 8, under specific experimental circumstances [dosage: 20 mg; concentration: 100 mg/L; duration: 120 min; temperature: 20° C.; volume: 50 mL], the impact of pH on the loading characteristics of OXPN into ZPh/HPA$_{NRs}$ and CH@ZPh/HPA$_{NRs}$ was evaluated.

Figure 6A:
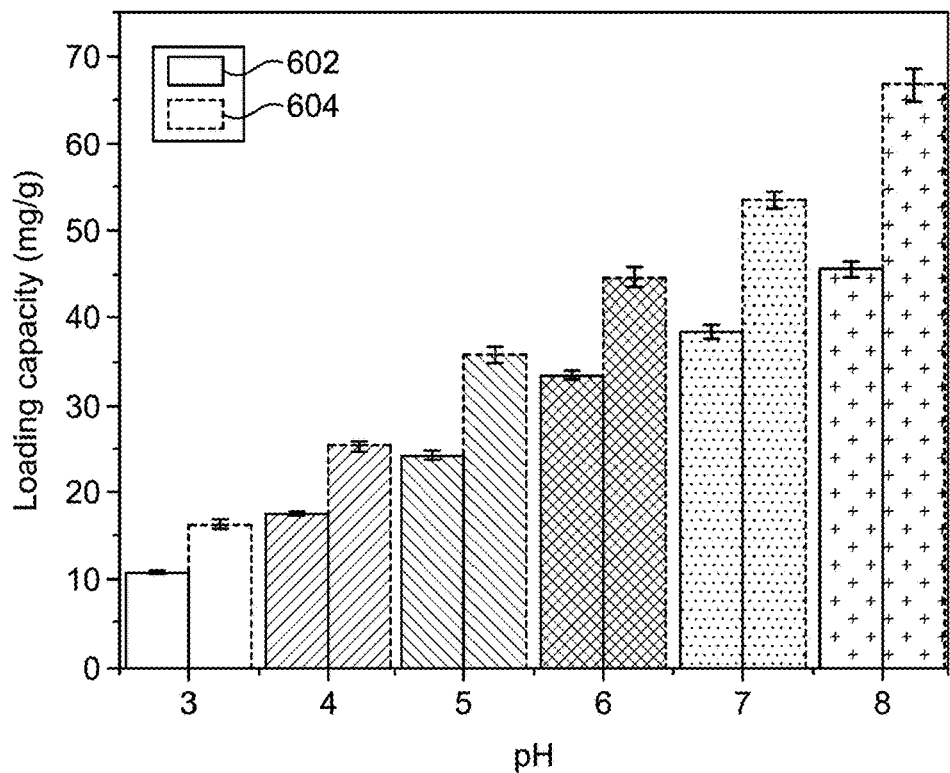
FIG. 6A illustrates an effect of pH on the loading of OXPN into ZPh/HPA$_{NRs}$ and CH@ZPh/HPA$_{NRs}$, according to certain embodiments.

FIG. 6A illustrates the effect of the loading parameters on the loading of OXPN into ZPh/HPA$_{NRs}$ (602) and CH@ZPh/HPA$_{NRs}$ (604). From pH 3 (10.8 mg/g for ZPh/HPA$_{NRs}$ (602) and 16.4 mg/g for CH@ZPh/HPA$_{NRs}$ (604) to pH 8 (45.4 mg/g for ZPh/HPA$_{NRs}$ (602) and 66.8 mg/g for CH@ZPh/HPA$_{NRs}$ (604), the OXPN loading characteristics of ZPh/HPA$_{NRs}$ (602) and CH@ZPh/HPA$_{NRs}$ (604) experimentally increased.

The loading mechanisms of OXPN into ZPh/HPA$_{NRs}$ (602) and CH@ZPh/HPA$_{NRs}$ (604) were, therefore, favored under basic conditions. In general, the pH of the solutions has an impact on both the ionization characteristics of the soluble OXPN molecules and the surficial charges of ZPh/HPA$_{NRs}$ (602) and CH@ZPh/HPA$_{NRs}$ (604). The OXPN structure has strong solubility and mobility characteristics at low pH levels, which negatively impairs the loading qualities under these circumstances. Additionally, the positively charged dissolved species of OXPN ([Pt(dach)(H$_2$O)Cl]$^+$ and [Pt(dach)(H$_2$O)$_2$]$^{2+}$) in the acidic environment demonstrate competitive and electrostatic repulsion behaviors with the hydronium ions that exist on the surfaces of ZPh/HPA$_{NRs}$ (602) and CH@ZPh/HPA$_{NRs}$ (604). Therefore, during the loading of OXPN into ZPh/HPA$_{NRs}$ and CH@ZPh/HPA$_{NRs}$, the basic condition is preferred, which is in accordance with the detected pH(PZC) values of ZPh/HPA$_{NRs}$ (pH=6.7) and CH@ZPh/HPA$_{NRs}$ (pH=6.3).

Figure 6B:
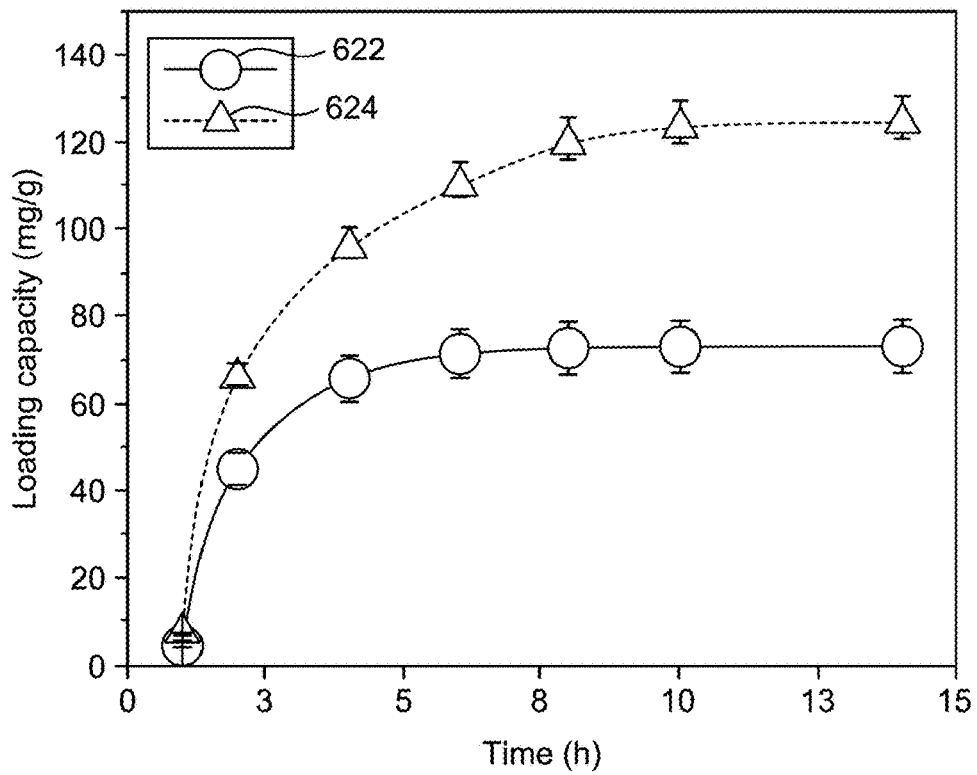
FIG. 6B illustrates the effect of loading duration on the loading of OXPN into ZPh/HPA$_{NRs}$ and CH@ZPh/HPA$_{NRs}$, according to certain embodiments.

Loading duration: The effects of the time duration on the loading characteristics of OXPN into ZPh/HPA$_{NRs}$ and CH@ZPh/HPA$_{NRs}$ were evaluated at regular intervals between 1 hour and 14 hours under specific conditions during experiments [dosage: 20 mg; concentration: 100 mg/L; pH 8; temperature: 20° C.; volume: 50 mL]. FIG. 6B illustrates the actual OXPN loading properties of ZPh/HPA$_{NRs}$ (622) and CH@ZPh-HPA$_{NRs}$ (624), demonstrating an increase in either the recognized rate or the loaded quantities in mg/g as the evaluated contact period is systematically expanded. In the presence of ZPh/HPA$_{NRs}$ (622) and CH@ZPh/HPA$_{NRs}$ (624), this increase in activity was observed for up to 6 hours and 10 hours, respectively. The experimentally obtained OXPN loading rate and the loaded quantity do not vary or are almost fixed after the previously described loading periods.

The presence of such consistent loading qualities verifies the equilibrium modes of the tested carriers (ZPh/HPA$_{NRs}$ (73.6 mg/g) and CH@ZPh/HPA$_{NRs}$ (125.3 mg/g)). At the beginning of the loading periods, the outer surfaces of ZPh/HPA$_{NRs}$ and CH@ZPh/HPA$_{NRs}$ exhibited an enormous number of sites that were active and free, which led to a noticeably high loading rate and an immediate rise in the OXPN loaded amounts. With increasing test durations, OXPN is gradually loaded into the free sites of ZPh/HPA$_{NRs}$ (622) and CH@ZPh/HPA$_{NRs}$ (624), causing consumption of these sites and a sharp drop in their accessibility. As a result, the OXPN loading rates decreased with time, and the experimental capacities of the carriers were minimized. After all of the available sites had been fully occupied by OXPN molecules, the equilibrium states of ZPh/HPA$_{NRs}$ (622) and CH@ZPh/HPA$_{NRs}$ (624) had been identified, and their surfaces were unable to receive any more ions.

OXPN concentration: The effect of initial OXPN concentration on the loading qualities of OXPN into ZPh/HPA$_{NRs}$ and CH@ZPh/HPA$_{NRs}$ was studied under specific conditions of experimentation [dosage: 20 mg; duration: 14 h; pH 8; temperature: 20° C.; volume: 50 mL]. The initial concentration as an investigated factor during an assessment of any examined carrier's loading qualities provides information for describing the equilibrium characteristics and determining the carrier's highest loading capacity.

Figure 6C:
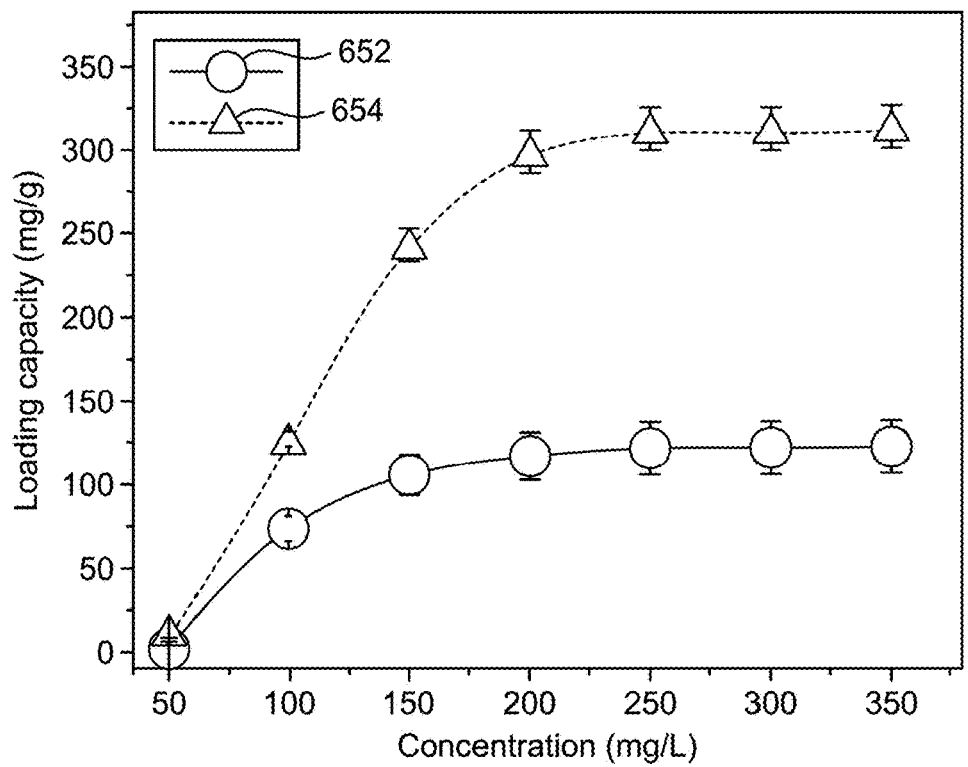
FIG. 6C illustrates the effect of OXPN starting concentration on the loading of OXPN into ZPh/HPA$_{NRs}$ and CH@ZPh/HPA$_{NRs}$, according to certain embodiments.

FIG. 6C illustrates the actual loading amounts of OXPN into ZPh/HPA$_{NRs}$ (652) and CH@ZPh/HPA$_{NRs}$ (654) were greatly increased once the experiments were performed in the presence of high levels of OXPN. The elevated level of OXPN as ions that dissolve in specific volumes causes a substantial rise in the mobility, diffusion, and acquired driving forces of these ions, which leads to collision and chemical contact with the distributed active sites on the outside surfaces of ZPh/HPA$_{NRs}$ (652) and CH@ZPh/HPA$_{NRs}$ (654) and thus the effectiveness of the loading process. This increase in the quantity of encapsulated OXPN in terms of beginning concentration may be observed up to 250 mg/L utilizing both ZPh/HPA$_{NRs}$ (652) and CH@ZPh/HPA$_{NRs}$ (654) carriers. The results of the tests that were executed in the presence of OXPN concentrations above those previously stated levels revealed a fixed loaded amount that indicated the equilibrium or saturated states of the used carriers. Thus, the integrated ZPh/HPA$_{NRs}$ (652) and CH@ZPh/HPA$_{NRs}$ (654) particles as carriers reach their true maximal OXPN loading capacities (122 mg/g for ZPh/HPA$_{NRs}$ and 311.4 mg/g for CH@ZPh/HPA$_{NRs}$. The notable high OXPN loading characteristics of CH@ZPh/HPA$_{NRs}$ particles in comparison with ZPh/HPA$_{NRs}$ particles are attributed to (1) the increased surface area of the CH@ZPh/HPA$_{NRs}$, (2) the organophilic properties of the composite displaying enhanced affinities for the organic molecules that comprise OXPN, and (3) a substantial rise in the total number of active sites owing to the integration of extra active chemical groups.

Figure 6D:
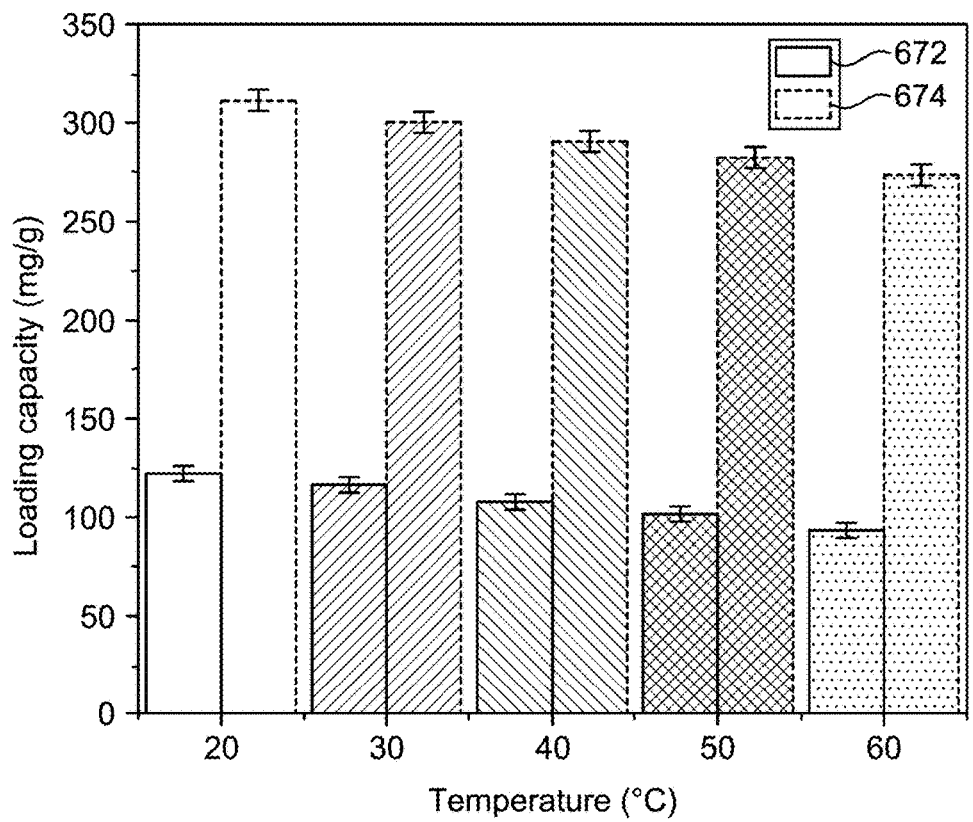
FIG. 6D illustrates the effect of loading temperature on the loading of OXPN into ZPh/HPA$_{NRs}$ and CH@ZPh/HPA$_{NRs}$, according to certain embodiments.

Effect of the loading temperature: FIG. 6D illustrates the drug loading assays conducted with a continuous elevation of temperature from 20 to 60° C. to ascertain if the temperature aided or hindered the loading properties of ZPh/HPA$_{NRs}$ (672) and CH@ZPh/HPA$_{NRs}$ (674) for OXPN. At 14 hours (the loading duration), 350 mg/L (OXPN concentrations), 20 mg (the dosage), pH 8 (the loading pH), and 50 mL (the total volume), the loading variables were adjusted. FIG. 6D illustrates the loading characteristics of ZPh/HPA$_{NRs}$ (672) and CH @ZPh/HPA$_{NRs}$ (674) for OXPN decrease as the loading temperature increases, which demonstrates the exothermic behavior of the loading mechanisms. The measured loading capacities for OXPN into ZPh/HPA$_{NRs}$ (672) and CH@ZPh/HPA$_{NRs}$ (674) at 60° C. are 93.3 and 273.3 mg/g, respectively. The CH@ZPh/HPA$_{NRs}$ composite has attractive qualities as a carrier for OXPN as a consequence of its high loading characteristics, according to the findings of loading studies. Furthermore, by adjusting different loading variables like pH, duration, drug concentration, and temperature, it is possible to regulate the amounts of drugs loaded onto CH@ZPh/HPA$_{NRs}$.

Figure 7A:
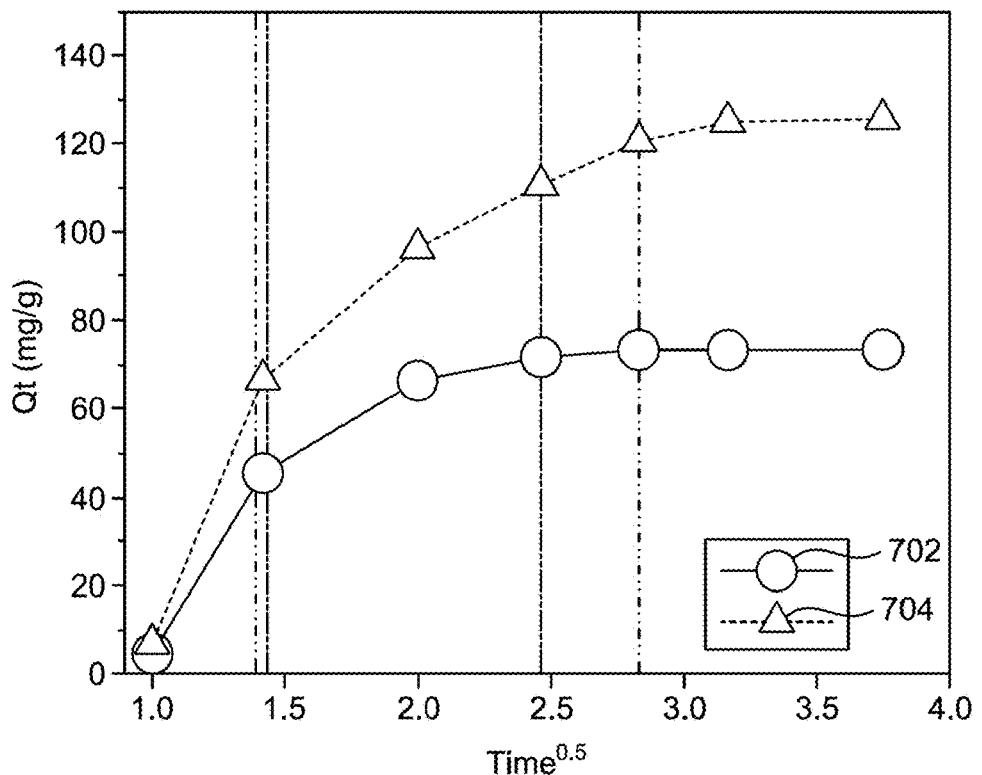
FIG. 7A illustrates the intra-particle diffusion curves of OXPN loading results, according to certain embodiments.

Intra-particle diffusion properties: FIG. 7A illustrates determining what influences loading mechanisms, the intra-particle diffusion behavior of OXPN loading onto ZPh/HPA$_{NRs}$ (702) and CH@ZPh/HPA$_{NRs}$ (704) has been assessed. The established curves display multi-linear (segmental) features that do not cross over at the origin. The outcomes of OXPN loading demonstrate that multistep regulating mechanisms rather than just the intra-particle diffusion process control the loading activities onto ZPh/HPA$_{NRs}$ (702) and CH@ZPh/HPA$_{NRs}$ (704). The tested carriers' acquired curves demonstrate that three consecutive controlling stages-external surface adsorption, intra-particle diffusion, and saturation stages-occurred throughout the loading activities (FIG. 7A).

The first noticeable segment is a representation of the outer surface adsorption stage. The availability of the active loading sites on the ZPh/HPA$_{NRs}$ (702) and CH@ZPh/HPA$_{NRs}$ (704) surfaces primarily affects this step. The second part is the intra-particle diffusion stage. During this stage, drug ions flow into the internal pores of the ZPh/HPA$_{NRs}$ (702) and CH@ZPh/HPA$_{NRs}$ (704) and bind to the internal loading sites with little help from the external loading sites. The equilibration and saturation stages, which make up the third and last segments, demonstrate a minimal to nonexistent improvement in the loading capacities of ZPh/HPA$_{NRs}$ and CH@ZPh/HPA$_{NRs}$ for the OXPN under consideration. The successful completion of the equilibration stage is attributed to the full saturation of all loading receptors and the growth of densely loaded layers of OXPN on the exterior of ZPh/HPA$_{NRs}$ and CH@ZPh/HPA$_{NRs}$ by means of molecular associations and inter-ionic attraction.

Figure 7B:
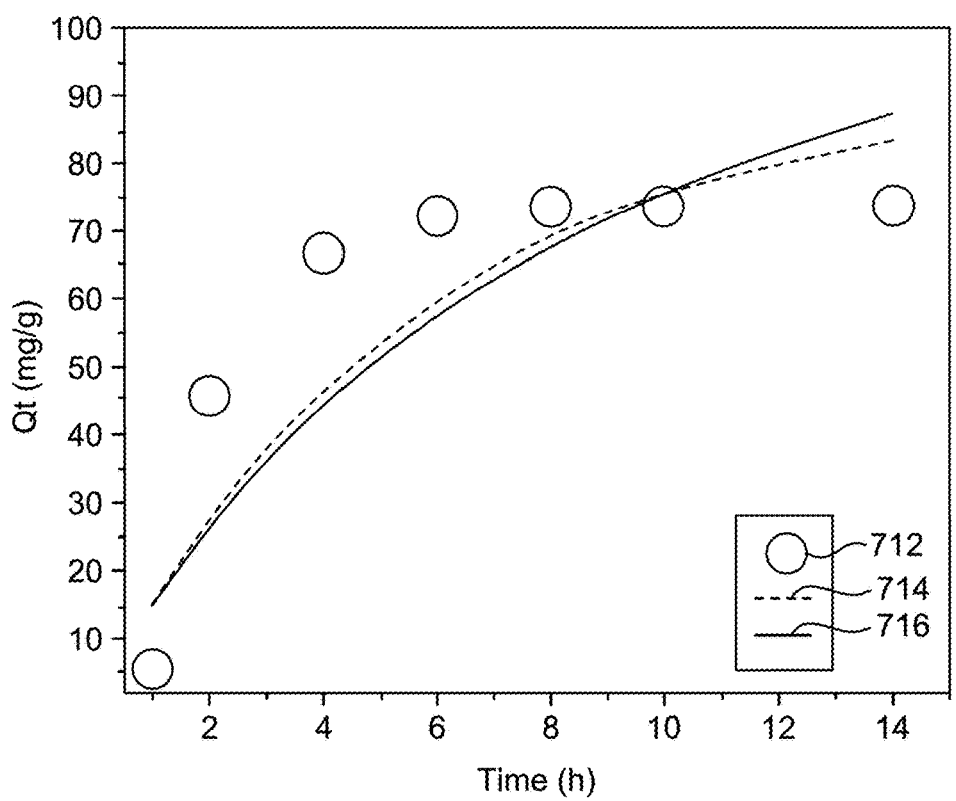
FIG. 7B illustrates the fitting of the OXPN loading results into ZPh/HPA$_{NRs}$ with the kinetic models, according to certain embodiments.
Figure 7C:
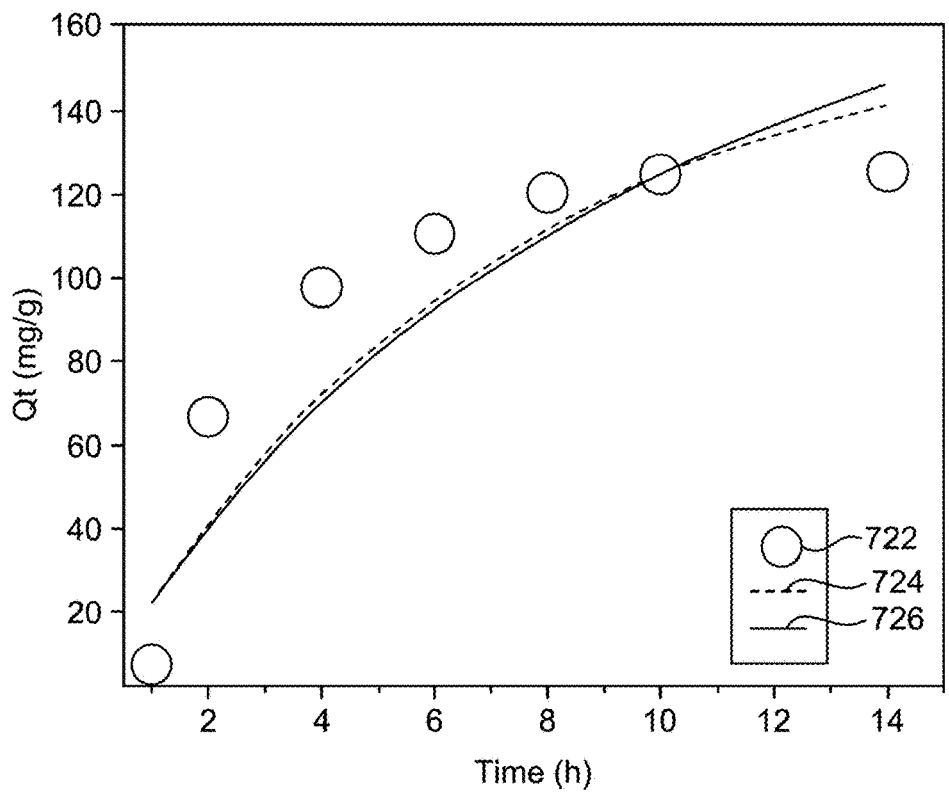
FIG. 7C illustrates the fitting of the OXPN loading results into CH@ZPh/HPA$_{NRs}$ with the kinetic models, according to certain embodiments.

Kinetic modeling: FIGS. 7B-7C illustrate fitting of the OXPN loading results into ZPh/HPA$_{NRs}$ with the mathematical parameters and hypotheses of the pseudo-first-order (PFO) (714, 724) (Eq. (4)) and pseudo-second-order (716, 726) (PSO) (Eq. (5)) models were used to investigate the kinetics of the loading activities of OXPN onto ZPh/HPA$_{NRs}$ 712 (FIG. 7B) and CH@ZPh/HPA$_{NRs}$ 722 (FIG. 7C). Non-linear fitting was employed to determine fit degrees by calculating the correlation coefficient ($R^2$) and Chi-square ($X^2$) values (Table 1).

$$Q_t = Q_e(1 - e^{-k_1 t}) \quad (4)$$

$$Q_t = \frac{Q_e^2 k_2 t}{1 + Q_e k_2 t} \quad (5)$$

TABLE 1

The theoretical parameters of the assessed kinetic, classical isotherm, advanced isotherm model, thermodynamic, and release kinetic models.

| Models | Parameters | Zph/HPA$_{NRs}$ | CH@ZPh/HPA$_{NRs}$ |
|---|---|---|---|
| Kinetic models | | | |
| Pseudo-First order | $K^1$ (min$^{-1}$) | 0.177 | 0.147 |
| | Qe (Cal) (mg/g) | 81.3 | 131.7 |
| | $R^2$ | 0.86 | 0.89 |
| | $X^2$ | 6.4 | 6.12 |

TABLE 1-continued

The theoretical parameters of the assessed kinetic, classical isotherm,
advanced isotherm model, thermodynamic, and release kinetic models.

| | | | |
|---|---|---|---|
| Pseudo-Second order | $K_2$ (g mg$^{-1}$ min$^{-1}$) | 8.1 × 10$^{-4}$ | 3.54 × 10$^{-4}$ |
| | $Q_e$ (Cal) (mg/g) | 141.6 | 259.9 |
| | $R^2$ | 0.81 | 0.85 |
| | $X^2$ | 7.06 | 9.2 |
| Classic isotherm models | | | |
| Langmuir | $Q_{max}$ (mg/g) | 133.6 | 345.6 |
| | b (L/mg) | 7.99 × 10$^{-7}$ | 2.49 × 10$^{-6}$ |
| | $R^2$ | 0.99 | 0.99 |
| | $X^2$ | 0.384 | 0.284 |
| | $R_L$ | 0.99 | 0.99 |
| Freundlich | 1/n | 0.20 | 0.71 |
| | $K_F$ (mg/g) | 119.8 | 308.5 |
| | $R^2$ | 0.99 | 0.99 |
| | $X^2$ | 0.136 | 0.491 |
| D-R model | β (mol$^2$/KJ$^2$) | 0.0092 | 0.0075 |
| | $Q_m$ (mg/g) | 143.8 | 354.2 |
| | $R^2$ | 0.95 | 0.81 |
| | $X^2$ | 4.5 | 8.2 |
| | E (KJ/mol) | 7.34 | 8.13 |
| Monolayer model of one energy | n | 6.8 | 9.3 |
| | Nm (mg/g) | 18.7 | 34.6 |
| | $Q_{(sat)}$ (mg/g) | 127.2 | 321.7 |
| | ΔE (kJ/mol) | −6.3 | −8.7 |
| Thermodynamics | | | |
| ΔG° (kJ/mol) | 293.15 | −12.07 | −15.06 |
| | 298.15 | −12.3 | −15.43 |
| | 303.15 | −12.51 | −15.81 |
| | 308.15 | −12.73 | −16.20 |
| | 313.15 | −12.87 | −16.57 |
| ΔH° (kJ/mol) | | −6.22 | −3.9 |
| ΔS° (J K$^{-1}$ mol$^{-1}$) | | 14.7 | 22.7 |

| | Determination coefficient ($R^2$) | | | |
|---|---|---|---|---|
| | ZPh/HPA$_{NRs}$ | | CH@ZPh/HPA$_{NRs}$ | |
| Models | Acetate buffer (pH 5.5) | Phosphate buffer (pH 7.4) | Gastric fluid (pH 1.2) | Intestinal fluid (pH 7.4) |
| Zero-order model | 0.90 | 0.93 | 0.65 | 0.78 |
| First-order model | 0.99 | 0.99 | 0.99 | 0.99 |
| Higuchi model | 0.94 | 0.97 | 0.90 | 0.93 |
| Hixson-Crowell | 0.98 | 0.96 | 0.91 | 0.97 |
| Krosmeyer-model | 0.92 | 0.89 | 0.88 | 0.91 |
| Peppas model n | 0.60 | 0.76 | 0.52 | 0.67 |

The OXPN loading processes into ZPh/HPA$_{NRs}$ and CH@ZPh/HPA$_{NRs}$ operated according to the kinetic characteristics of the PFO model instead of the PSO model, as determined by the established $R^2$ and $X^2$ values. The conformity of these results with the kinetic characteristics of PFO was supported by the noticed agreement between the established experimental results (73.6 mg/g (ZPh/HPA$_{NRs}$) and 125.3 mg/g (CH@ZPh/HPA$_{NRs}$)) and the mathematically accomplished values of Qe as the theoretical parameters (81.3 mg/g (ZPh/HPA$_{NRs}$) and 131.7 mg/g (CH@ZPh/HPA$_{NRs}$) (Table 1). This kinetic behavior corresponds to physical loading mechanisms, which may involve the forces of van der Waals and/or electrostatic attraction. However, encapsulation mechanisms are more congruent with the PFO theory than the PSO hypothesis; the reactions that took place via ZPh/HPA$_{NRs}$ and CH@ZPh/HPA$_{NRs}$ still exhibit substantial fitting with the PSO model's illustrative equation. Consequently, several weak chemisorption operations (electron exchanges, hydrogen bonds, and chemical complexes) may serve a supporting role or have minimal impact during the loading of OXPN. The collaboration of complex mechanisms (physical and chemical) can be realized by generating layers of chemically loaded OXPN that serve as substrates for additional layers of loaded drugs via physical mechanisms.

Figure 7D:
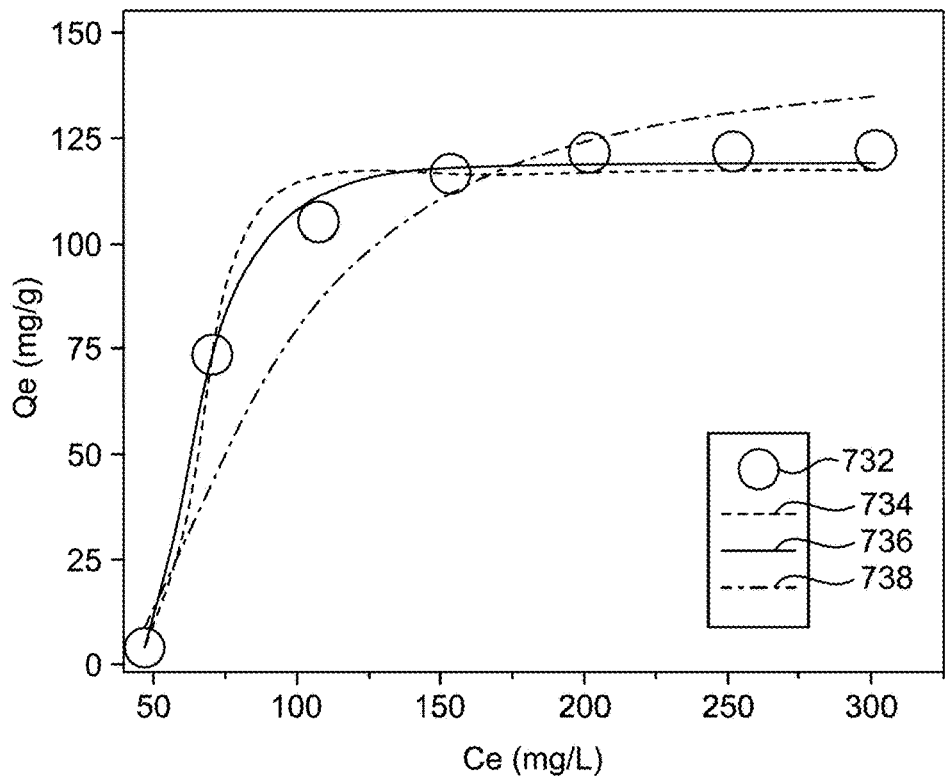
FIG. 7D illustrates the fitting of the OXPN loading results into ZPh/HPA$_{NRs}$ with the classic isotherm models, according to certain embodiments.
Figure 7E:
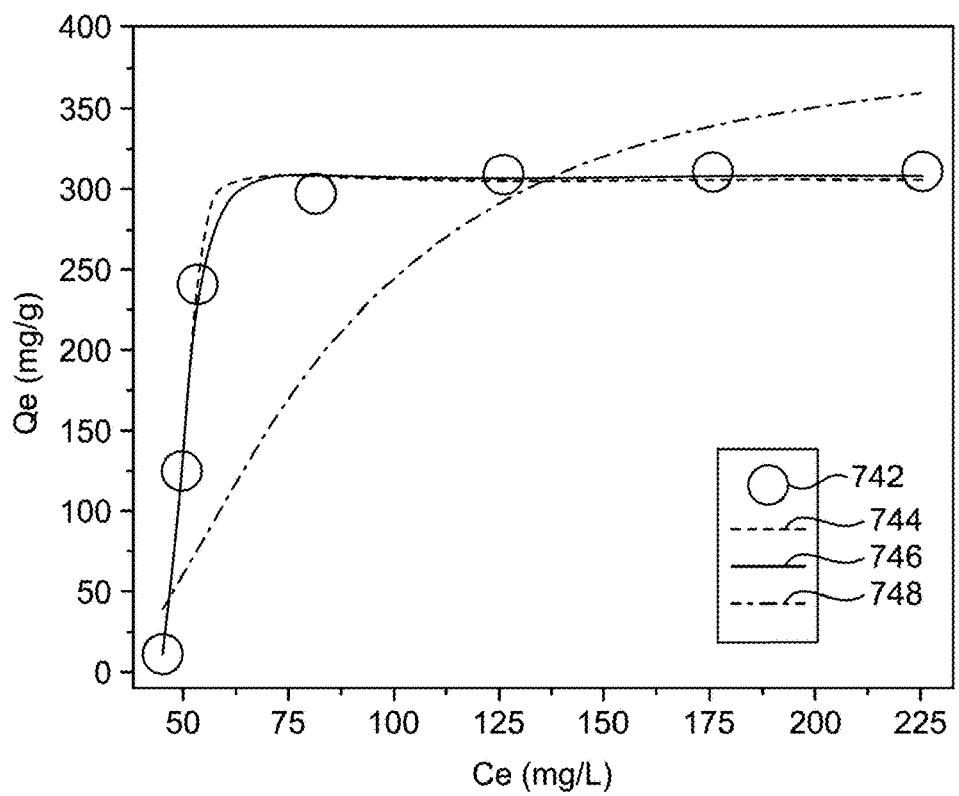
FIG. 7E illustrates the fitting of the OXPN loading results into CH@ZPh/HPA$_{NRs}$ with the classic isotherm models, according to certain embodiments.

Classic isotherm modeling: FIGS. 7D-7E illustrates three conventional isotherm models Langmuir (734, 744) (Eq. (6)), Freundlich (736, 746) (Eq. (7)), and Dubinin-Radushkevich (D-R) (738, 748) (Eq. (8)) used to evaluate the equilibrium properties of the OXPN loading mechanisms onto ZPh/HPA$_{NRs}$ (732) (FIG. 7D) and CH@ZPh/HPA$_{NRs}$ (742) (FIG. 7E). $R^2$ and $X^2$ values were identified using nonlinear fitting as the basis to determine the degree of fit (Table 1).

$$Q_e = \frac{Q_{max}bC_e}{(1+bC_e)} \quad (6)$$

$$Q_e = K_f C_e^{1/n} \quad (7)$$

$$Q_e = Q_m e^{-\beta e^2} \quad (8)$$

The values of $R^2$ and $X^2$ show that, as compared to the Langmuir model, the Freundlich isotherm hypothesis more accurately describes the results of the loading mechanisms of OXPN onto ZPh/HPA$_{NRs}$. This finding demonstrates that heterogeneous and multilayer loading represents the majority of OXPN loading processes. The functionalization of chitosan slightly affects the equilibrium properties of the OXPN loading reactions onto CH@ZPh/HPA$_{NRs}$. The results demonstrate a slightly higher agreement between the loading properties of the CH@ZPh/HPA$_{NRs}$ composite and the isotherm assumption of the Langmuir model, demonstrating homogenous loading behaviors in monolayer forms. Additionally, the Langmuir model's expected values of RL (the equilibration factor) are smaller than one, showing that OXPN has favorable loading features onto ZPh/HPA$_{NRs}$ and CH@ZPh/HPA$_{NRs}$ (Table 1). According to the Langmuir isotherm analysis, the anticipated maximal loading capacities ($Q_{max}$) of OXPN onto ZPh/HPA$_{NRs}$ and CH@ZPh/HPA$_{NRs}$ are 133.6 mg/g and 345.6 mg/g, respectively. The D-R model is particularly effective in revealing the energetic heterogeneity of ZPh/HPA$_{NRs}$ and CH@ZPh/HPA$_{NRs}$ that occurs during the OXPN loading activities, irrespective of the homogeneity or heterogeneity of their surfaces.

The D-R model's Gaussian energy (E), which is obtained mathematically, provides an insight in identifying the type of mechanisms that were participating during the loading of OXPN, whether they are physical or chemical in origin. Strong physical processes are operating when E values are <8 KJ/mol, while mild chemical or complex physical/chemical processes are operating when E values are between 8 and 16 KJ/mol. E values over 16 KJ/mol for loading processes are a sign of strong chemical mechanisms. The established values of E for both loading activities of OXPN by ZPh/HPA$_{NRs}$ and CH@ZPh/HPA$_{NRs}$ are 7.34 KJ/mol and 8.13 KJ/mol, respectively (Table 1). The E values demonstrated the involvement of intricate physical/chemical mechanisms in the OXPN loading processes and were influenced by weak chemical processes, especially after the integration of the chitosan chains.

Figure 7F:
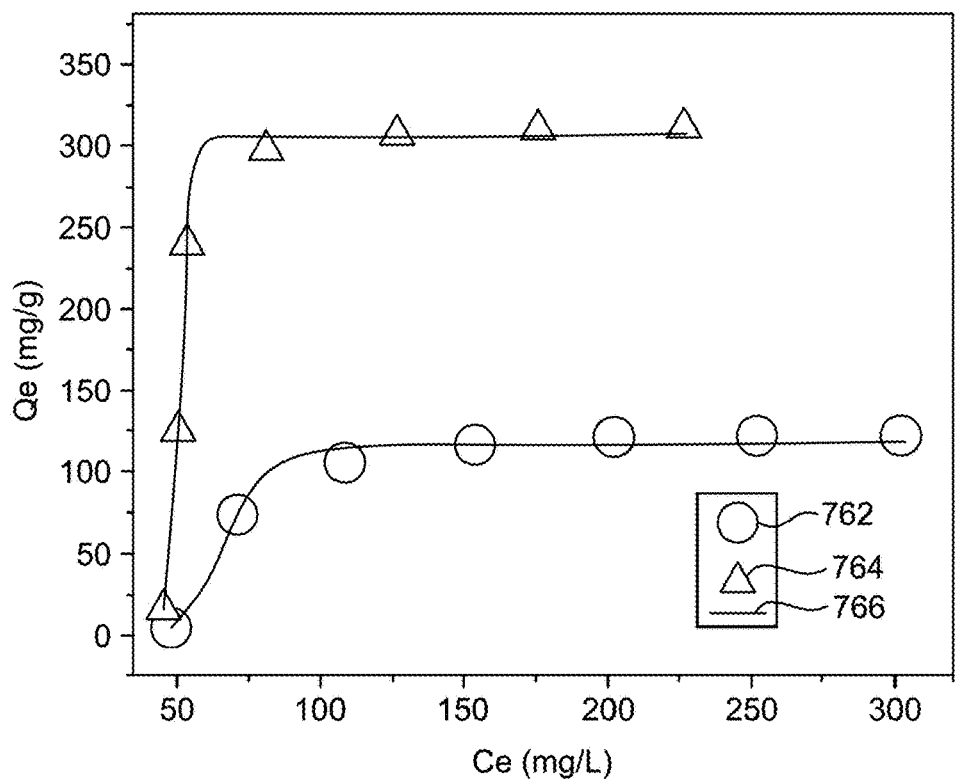
FIG. 7F illustrates the fitting of the OXPN loading results into ZPh/HPA$_{NRs}$ and CH@ZPh/HPA$_{NRs}$ with the monolayer model of one energy, according to certain embodiments.

Advanced equilibrium studies: On the basis of statistical physics, advanced isotherm (equilibrium) models were studied to ascertain how OXPNs are loaded onto ZPh/HPA$_{NRs}$ and CH@ZPh/HPA$_{NRs}$. FIG. 7F illustrates the representative model for fitting the OXPN loading data (Table 1) was the monolayer model of one energy site (Eq. (9)), which had the highest R$^2$ and lowest root mean square error (RMSE).

$$Q = nN_0 = \frac{nN_M}{1+\left(\frac{c_{1/2}}{C_e}\right)^n} = \frac{Q_o}{1+\left(\frac{C_{1/2}}{C_e}\right)^n} \tag{9}$$

The monolayer model of one energy site's mathematical parameters was established in order to clarify the overall loading mechanisms. The energetic (loading energy (E)) and steric (loading site density (Nm), number of loaded drug ions per one active site (n), and saturation loading capacity ($Q_{sat}$)) parameters are displayed in Table 1. The values of the active site density (Nm) enhanced after the chitosan functionalization step, from 18.7 mg/g for ZPh/HPA$_{NRs}$ to 34.6 mg/g for CH@ZPh/HPA$_{NRs}$. This validates the notable impact of the integrated chitosan in inducing the quantities of the active sites during the loading reactions, which illustrate the markedly high loading capacity of CH@ZPh/HPA$_{NRs}$ composite at the saturation state ($Q_{sat}$=321.7 mg/g) as compared to ZPh/HPA$_{NRs}$ ($Q_{sat}$=127.2 mg/g). Also, the functionalization process resulted in an enhancement in the loading capacity of each active site; each active site on the surface of CH@ZPh/HPA$_{NRs}$ can be loaded with up to 10 molecules of OXPN, while each active site on the surface can be loaded with only 7 molecules of OXPN. Moreover, detecting a value of n larger than one demonstrates the operation of multi-molecular mechanisms during the loading of OXPN into ZPh/HPA$_{NRs}$ and CH@ZPh/HPA$_{NRs}$ in addition to the vertical orientations of the already loaded drug ions. Using Eq. (10), the loading energies (E) were determined to establish the type of loading mechanisms (chemical or physical) that influence the loading of OXPN onto ZPh/HPA$_{NRs}$ and CH@ZPh/HPA$_{NRs}$.

$$\Delta E = -RT\ln\left(\frac{S}{C_{1/2}}\right) \tag{10}$$

Figure 8:
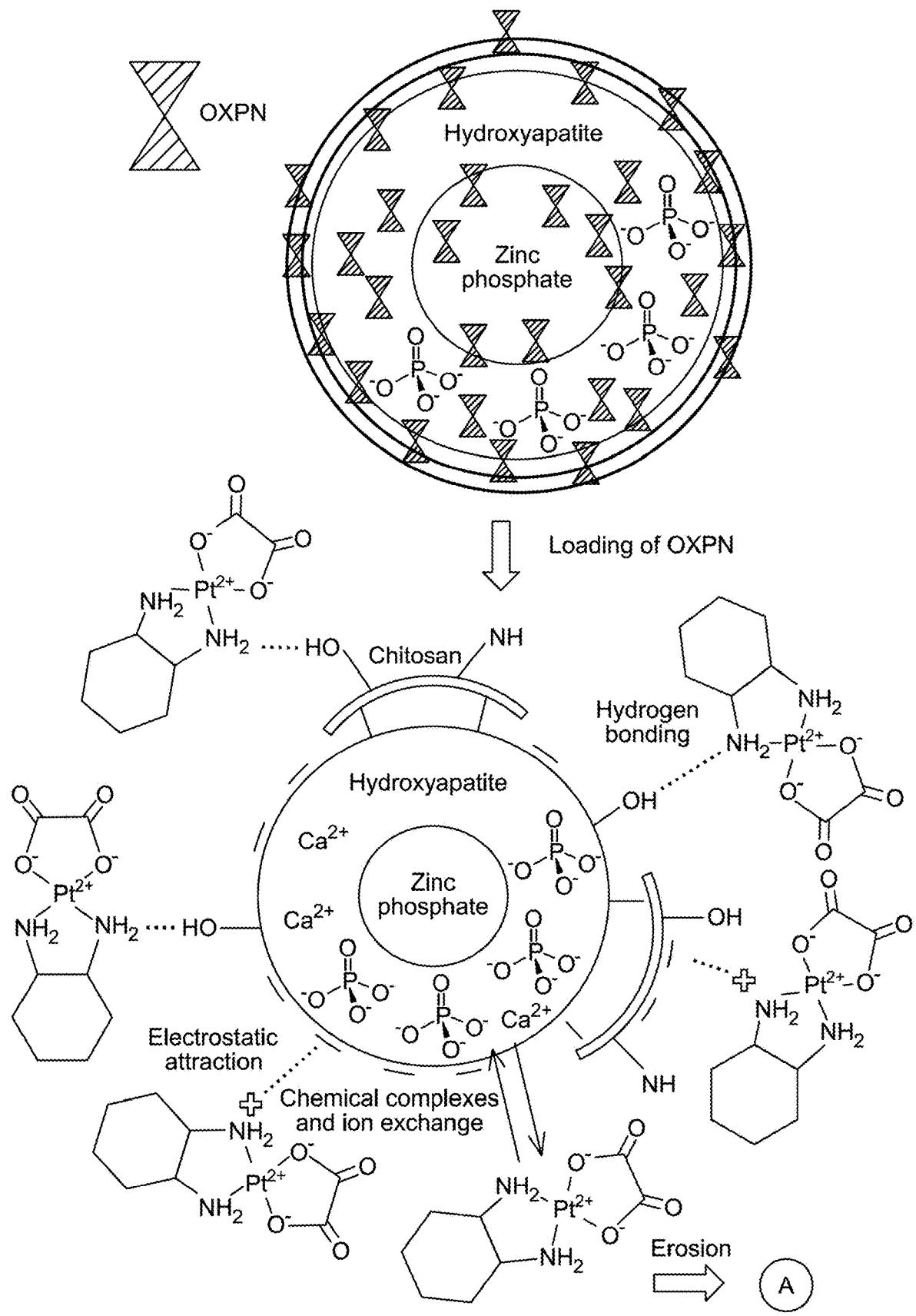
FIG. 8 illustrates a schematic diagram for the loading and release of OXPN from CH@ZPh/HPA$_{NRs}$ composite, according to certain embodiments.
Figure 8:
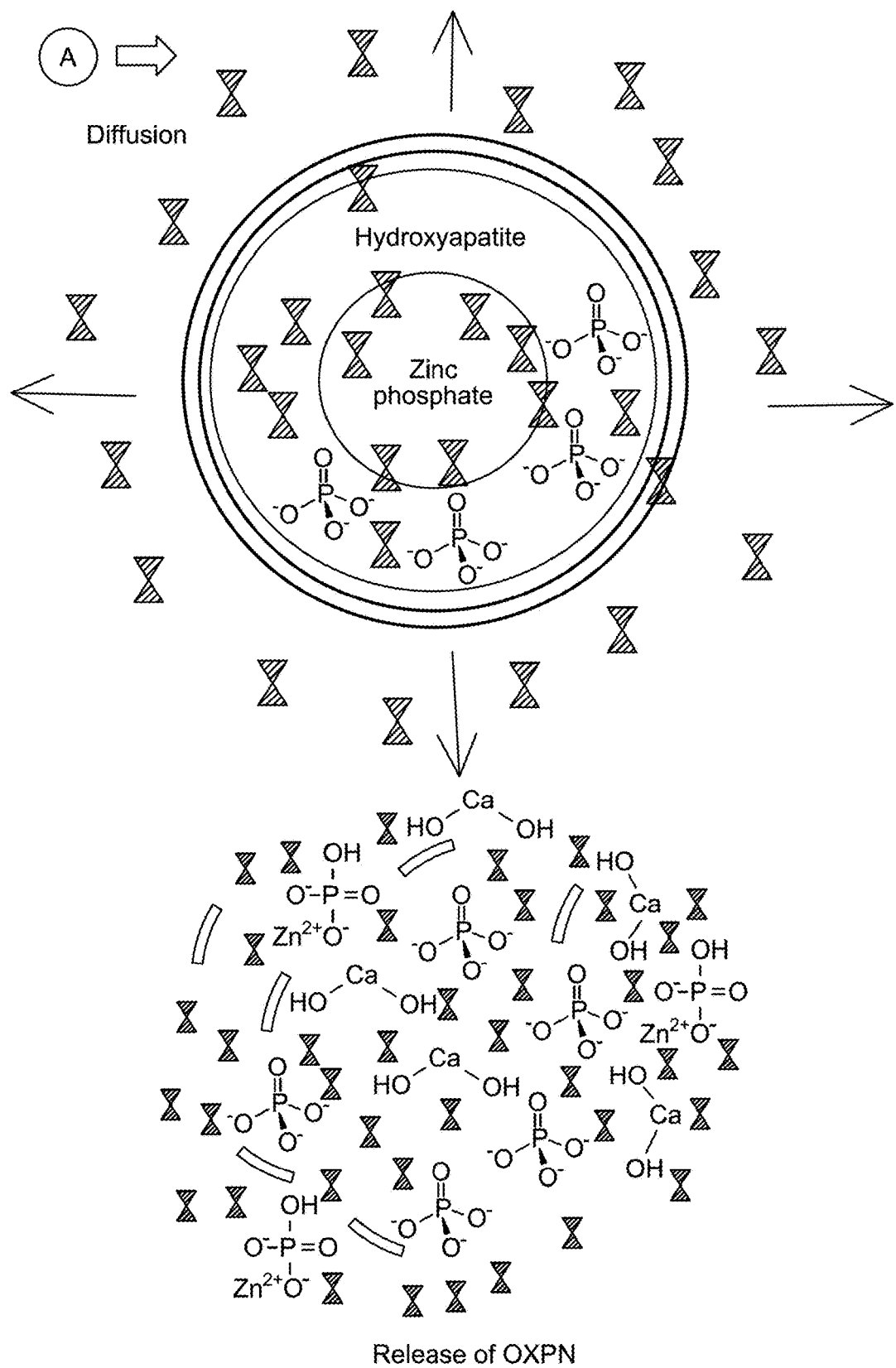

The loading energies of ZPh/HPA$_{NRs}$ and CH@ZPh/HPA$_{NRs}$ during the loading of OXPN were estimated to be −6.34 KJ/mol and −8.7 KJ/mol, respectively (Table 1). According to the previously stated values, physical loading mechanisms relating to van der Waals forces (E=4-10 kJ/mol), dipole bond forces (E=2-29 kJ/mol), electrostatic interactions (E=2-50 kJ/mol), and hydrogen bonds (E=30 kJ/mol) were indicated for the loading of OXPN into ZPh/HPA$_{NRs}$ and CH@ZPh/HPA$_{NRs}$. FIG. 8 illustrates the general loading mechanisms based on the energetic studies that were presented schematically.

Figure 9:
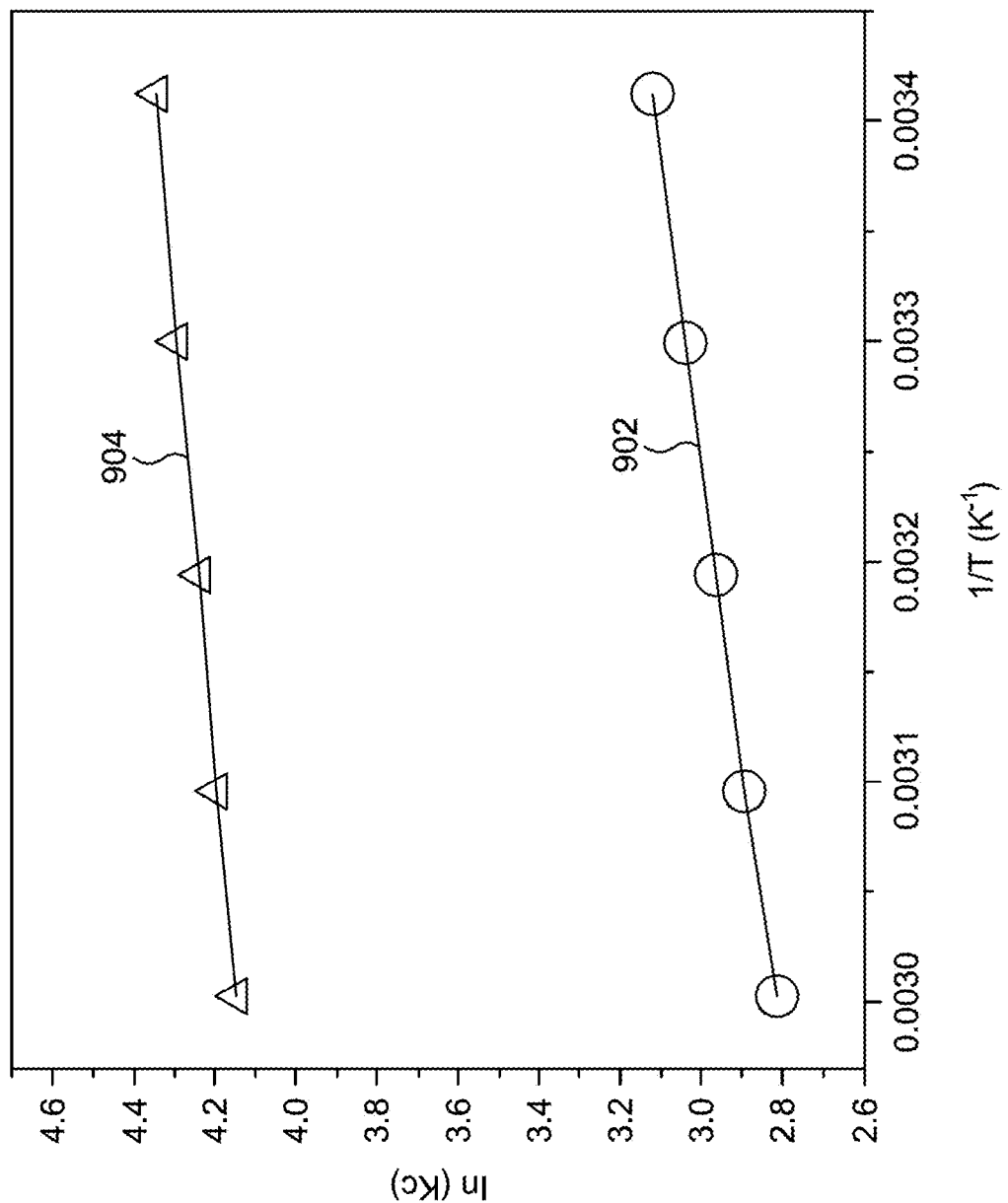
FIG. 9 illustrates the fitting of the OXPN loading results with Van't Hof thermodynamic equation, according to certain embodiments.

Thermodynamic properties: Thermodynamic tests for OXPN loading onto ZPh/HPA$_{NRs}$ and CH@ZPh/HPA$_{NRs}$ were carried out at temperatures between 20° C. and 60° C. The loading conditions were selected: a loading pH value of 8, a concentration of 350 mg/L, a dose of 20 mg, and a solution volume of 50 mL. The study addressed entropy ($\Delta S°$), enthalpy ($\Delta H°$), and Gibbs free energy ($\Delta G°$) as the essential functions of the thermodynamic systems. FIG. 9 illustrates the Van't Hoff equation (Eq. (11)) subjected to linear regression analysis to determine the values of $\Delta H°$ and $\Delta S°$ while the values of $\Delta G°$ estimated using Eq. (12) (Table 1) in ZPh/HPA$_{NRs}$ (902) and CH@ZPh/HPA$_{NRs}$ (904).

$$\ln(K_c) = \frac{\Delta S°}{R} - \frac{\Delta H°}{RT} \tag{11}$$

$$\Delta G° = -RT\ln K_c \tag{12}$$

The results show that the loading chemical reactions of OXPN onto ZPh/HPA$_{NRs}$ and CH@ZPh/HPA$_{NRs}$ have negative $\Delta G°$ values, revealing that these processes occurred spontaneously and are thermodynamically favorable (Table 1). The determined values of $\Delta H°$ are negative, revealing that the loading processes of OXPN onto ZPh/HPA$_{NRs}$ and CH@ZPh/HPA$_{NRs}$ are exothermic in nature. The increase in temperature value results in a rise in the randomness of the OXPN loading reactions, which is specified by the positive signs of $\Delta S°$ values.

Example 10: Drug Release Properties

Figure 10A:
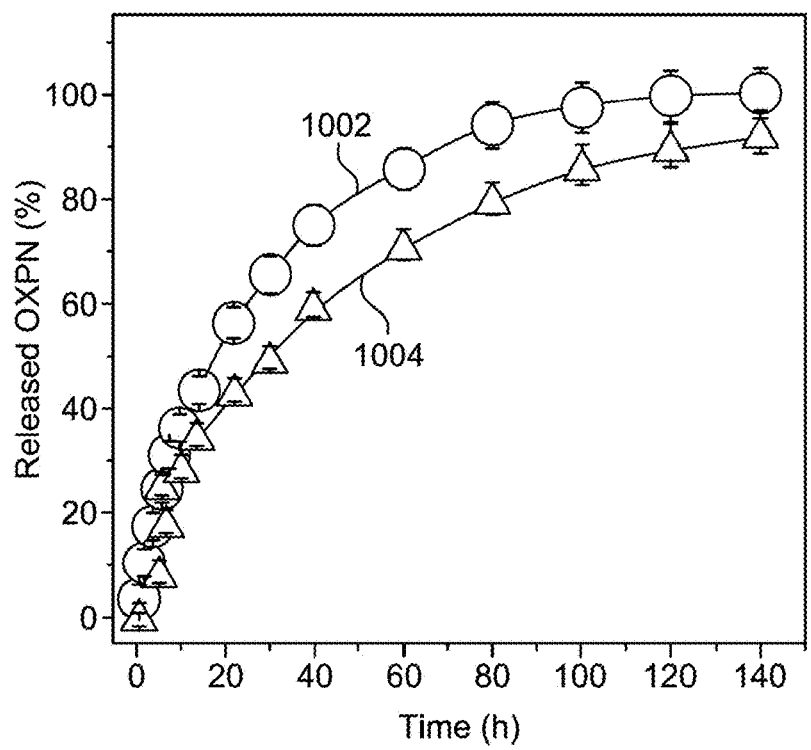
FIG. 10A illustrates the in-vitro release profiles of OXPN from ZPh/HPA$_{NRs}$, according to certain embodiments.
Figure 10B:
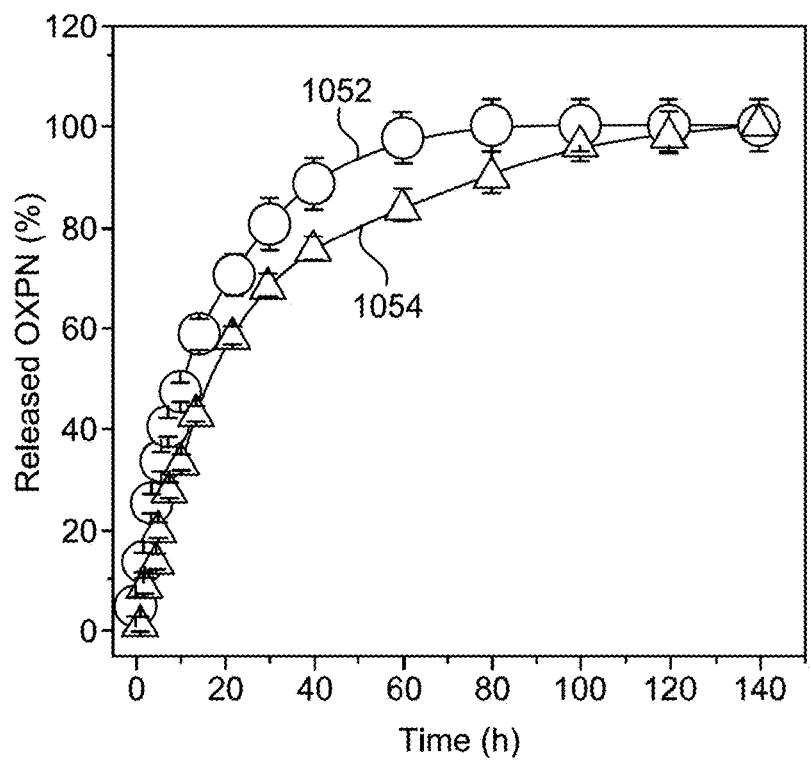
FIG. 10B illustrates the in-vitro release profiles of OXPN from CH@ZPh/HPA$_{NRs}$, according to certain embodiments.

In-vitro release profiles: FIGS. 10A-10B show the measured percentages of the OXPN molecules that were diffused within two selected buffers phosphate (1004, 1054) (pH 7.4) and acetate (1002, 1052) (pH 5.5) which were used to mimic the environment and circumstances of the cancerous cells, the OXPN release profiles of ZPh/HPA$_{NRs}$ (FIG. 10A) and CH@ZPh/HPA$_{NRs}$ (FIG. 10B) were assessed. The determined OXPN diffused % from both ZPh/HPA$_{NRs}$ and CH@ZPh/HPA$_{NRs}$ in the two investigated buffers verified obvious variations in the realized rates with a considerable increase in the evaluated release time. Both ZPh/HPA$_{NRs}$ and CH@ZPh/HPA$_{NRs}$ exhibit fast OXPN releasing rates within the starting release intervals, which were correlated with variations in the released OXPN values. The real OXPN diffusion rates decreased after a specific release period, and there was no discernible change in the release properties, which showed fixed behavior at the time at which the testing was complete.

The very rapid OXPN diffusion properties observed during the earliest release periods were attributed to the steady desorption of the drug instantaneously from the poorly bonded as well as physically adsorbed OXPN ions by the surficial sites of ZPh/HPA$_{NRs}$ and CH @ZPh/HPA$_{NRs}$. After the poorly bonded and surface loaded OXPN molecules were completely desorbed, the release performance was influenced mainly by the diffusion process of the strong chemically bonded ions and the formed complexes, as well as the entrapped OXPN ions inside the crystalline pores of hydroxyapatite, which have a negative impact on the measured diffusion rates. Furthermore, in contrast to basic circumstances (pH 7.4 (phosphate buffer)), the measured OXPN release behavior of ZPh/HPA$_{NRs}$ and CH@ZPh/HPA$_{NRs}$ showed a considerable accelerating effect of the acidic environment (pH 5.5 (acetate buffer)). The accelerated OXPN release properties at pH 5.5 versus pH 7.4 were attributed to an increase in the drug's solubility, mobility, and diffusion features as pH decreased. Furthermore, the predicted degrading impact of the low pH situation on the structure of the hydroxyapatite promotes quick-release properties.

FIG. 10A illustrates the experimentally determined OXPN release profiles of ZPh/HPA$_{NRs}$ at the phosphate or acetate buffers continued for approximately 100 hours without any actual identification of the fully released states. After 22 and 40 h at pH 5.5 (1002) and pH 7.4 (1004), respectively, approximately 50% of the entrapped amount of OXPN diffused out of the ZPh/HPA$_{NRs}$ structure. After 120 hours, the maximal percentages of OXPN released in the phosphate and acetate buffers are 92.2% and 100%, respectively.

FIG. 10B illustrates the profiles of CH@ZPh/HPA$_{NRs}$ exhibit faster release behaviors than ZPh/HPA$_{NRs}$. After 10 and 22 hours at pH 5.5 (1052) and pH 7.4 (1054), respectively, almost 50% of the entrapped amount of OXPN was released from the CH@ZPh/HPA$_{NRs}$ structure. However, the entirety of the release in the phosphate buffered solution was observed after 140 hours and the full release in that of the acetate buffer after roughly 80 hours.

The considerably higher OXPN release potential of CH@ZPh/HPA$_{NRs}$ demonstrates the influence of the incorporated chitosan chains on the physical and chemical properties of hydroxyapatite. The effectiveness of the release reactions of the entrapped ions is strongly adversely affected by the frequent creation of hydrogen bonds and chemical complexes between the active hydroxyl groups of the hydroxyapatite and functional groups of OXPN, besides the retention of the drug ions inside its porous framework. As a result, the modification of ZPh/HPA$_{NRs}$ with the chitosan chains creates barriers that exist between the medication and the reactive sites of the hydroxyapatite, reducing the total number of formed complexes and entrapped ions. Additionally, the interconnected chitosan chains supply more free active sites on the surface of the hydroxyapatite during the loading processes that also trigger the release qualities.

In some circumstances, continuous interaction and prolonged exposure between the medication ions and the cancerous cells are required. Therefore, delivery systems with gradual and controllable diffusion properties have been suggested. In some circumstances, therapeutic dosages must be administered at brief intervals; hence, very quick and sudden methods of delivery are strongly suggested. As a result, synthetic ZPh/HPA$_{NRs}$ and CH@ZPh/HPA$_{NRs}$ as prospective OXPN carriers can serve as favorable delivery systems with controlled encapsulation and release.

The evaluation of the kinetics of OXPN releasing processes from ZPh/HPA$_{NRs}$ and CH@ZPh/HPA$_{NRs}$ provides insight to establishing the basic release mechanisms. The linear equations describing the release kinetics of different kinetic models, such as the zero-order (Eq. (13)), first-order (Eq. (14)), Higuchi model (Eq. (15)), Hixson-Crowell model (Eq. (16)), and Korsmeyer-Peppas model (Eq. (17)), were linearly fitted to the in vitro release results.

$$W_t - W_0 = K_0 \cdot t \tag{13}$$

$$\ln(W_\infty / W_t) = K_1 \cdot t \tag{14}$$

$$W_t = K_h t^{1/2} \tag{15}$$

$$W_0^{1/3} - W_t^{1/3} = K_{HC} t \tag{16}$$

$$W_t / W_\infty = K_p t^n \tag{17}$$

Drug release reactions with zero-order kinetics possess a constant rate of release that is not influenced by the total amount of drug-loaded. The rates of drug release mechanisms that follow first-order kinetics display a substantial dependence on the amount of drug that has already been loaded. Drug diffusion is the primary release mechanism involved in drug release systems that adhere strongly to the Higuchi model. The Higuchi model proposes several concepts, including the constant nature of the loaded drug's diffusion in one direction, the existence of a significantly higher drug dosage versus the drug solubility, the minimal impact of the carrier dissolving and swelling, the persistence of adequate sink conditions during the release, and the substantial differences between the size of the drugs and the wall thickness of their carriers. The Hixson-Crowell model-based release systems state that the drug release mechanisms are influenced by the dimension and surface area of the carriers as well as the erosion processes.

Figure 11A:
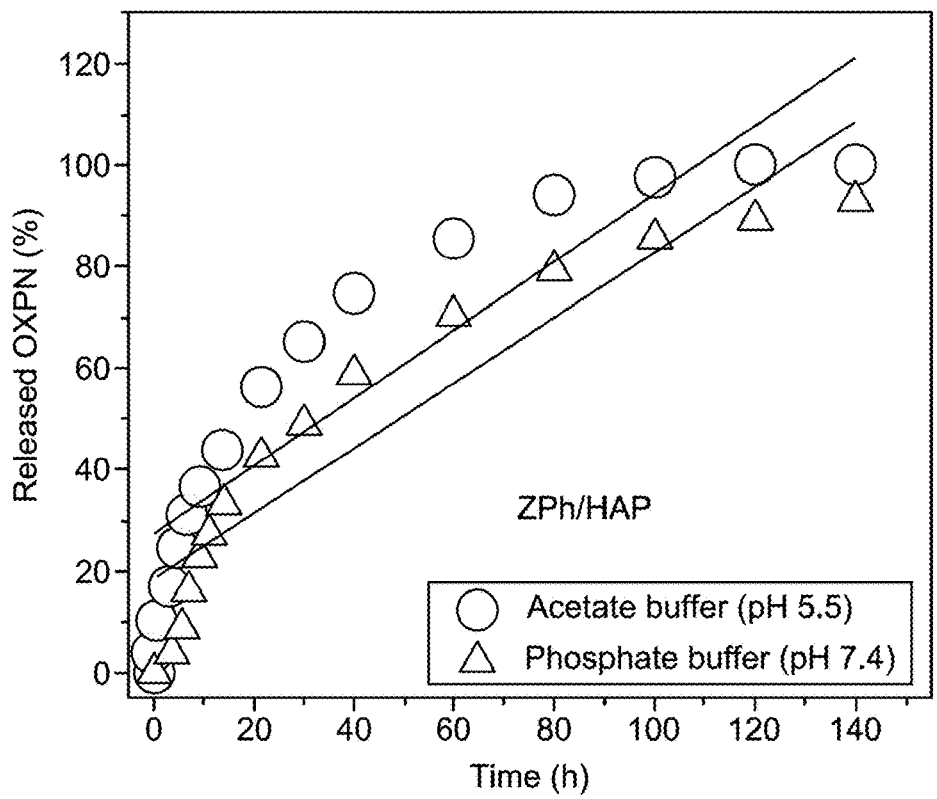
FIG. 11A illustrates the fitting of the OXPN release results with the zero-order model ZPh/HPA$_{NRs}$, according to certain embodiments.
Figure 11B:
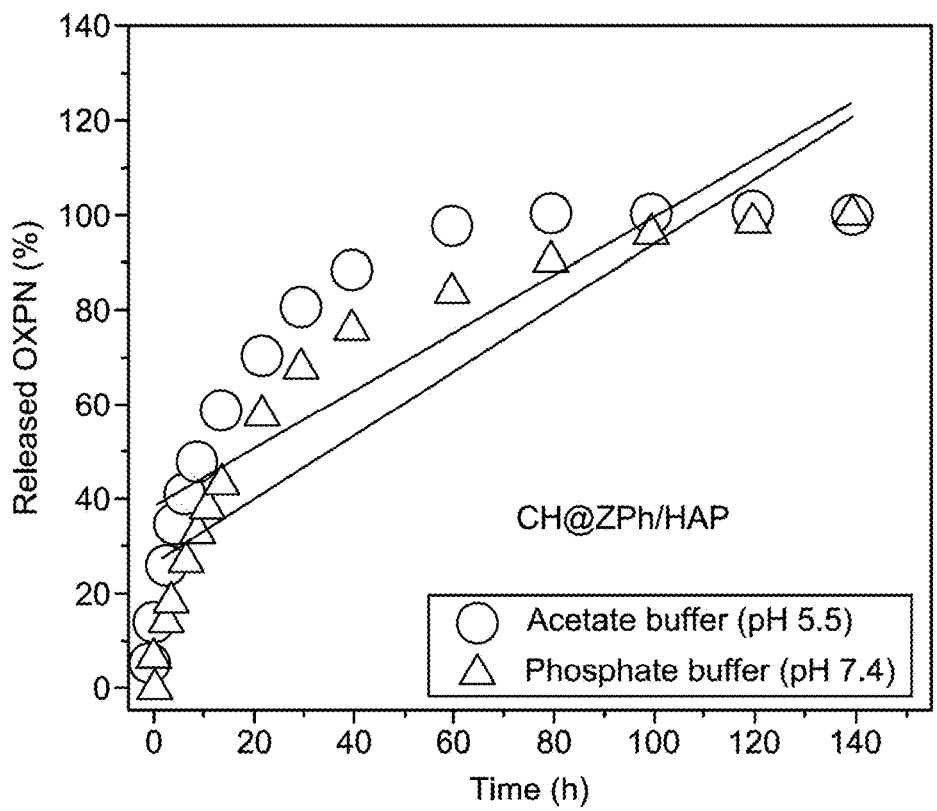
FIG. 11B illustrates the fitting of the OXPN release results with the zero-order model CH@ZPh/HPA$_{NRs}$, according to certain embodiments.
Figure 11C:
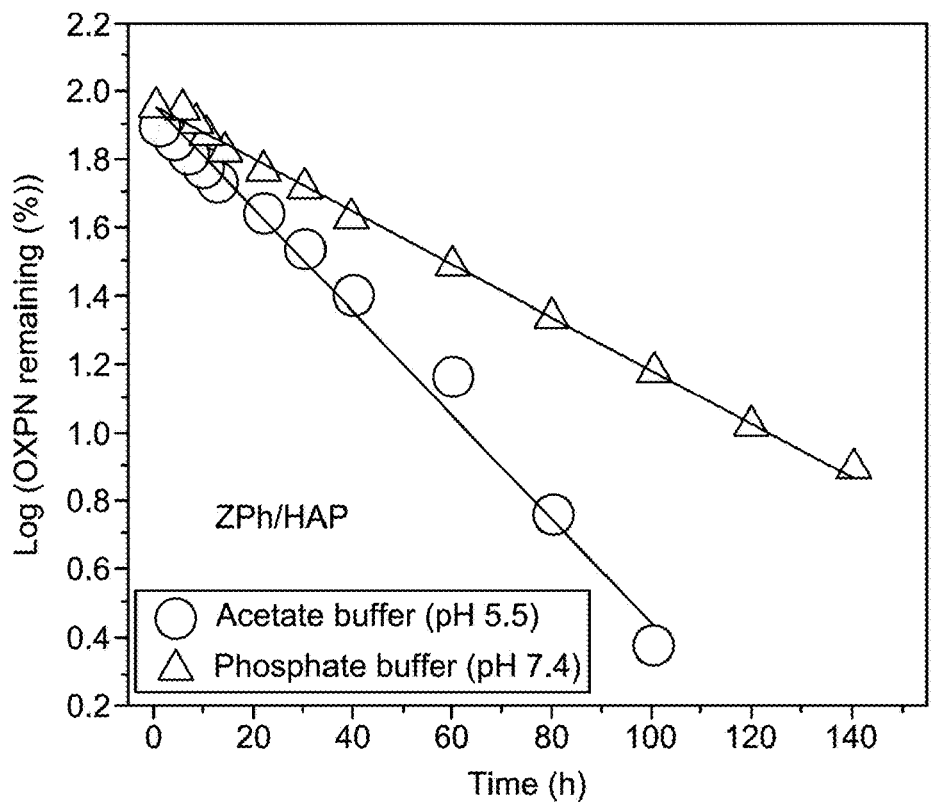
FIG. 11C illustrates the fitting of the OXPN release results with the first-order model ZPh/HPA$_{NRs}$, according to certain embodiments.
Figure 11D:
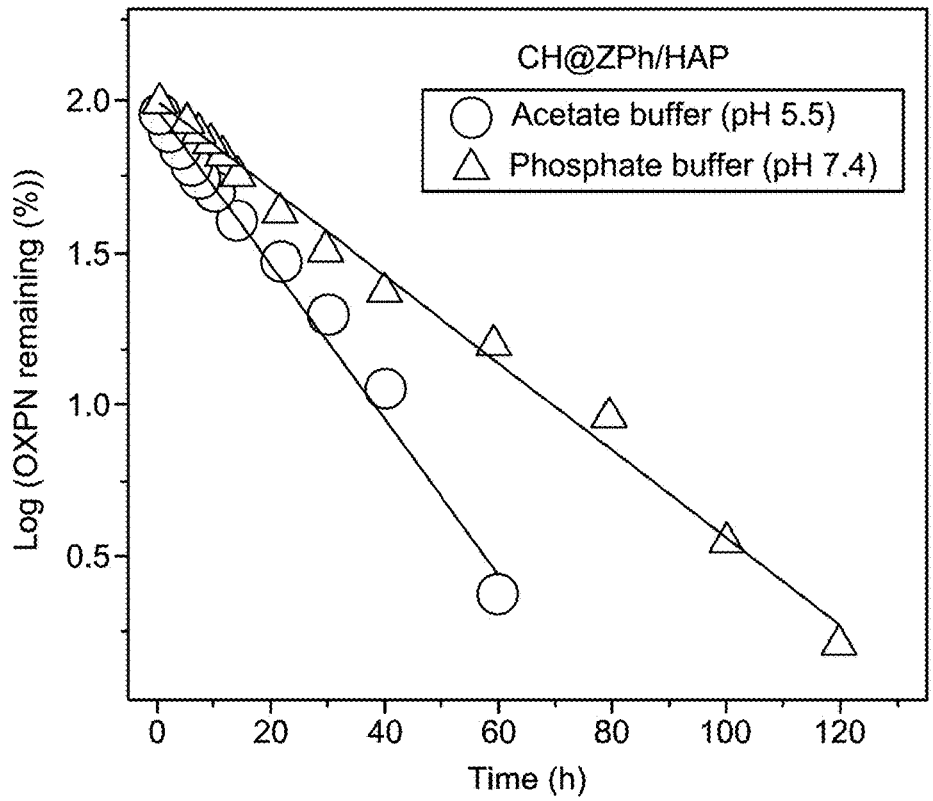
FIG. 11D illustrates the fitting of the OXPN release results with the first-order model CH@ZPh/HPA$_{NRs}$, according to certain embodiments.
Figure 11E:
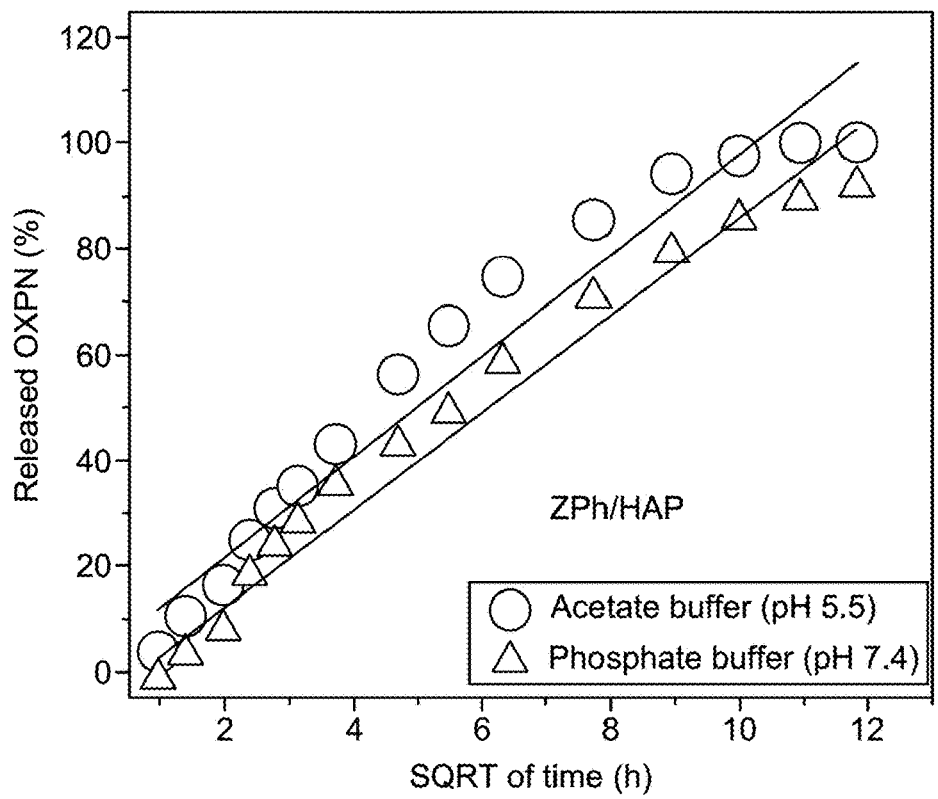
FIG. 11E illustrates the fitting of the OXPN release results with the Higuchi model ZPh/HPA$_{NRs}$, according to certain embodiments.
Figure 11F:
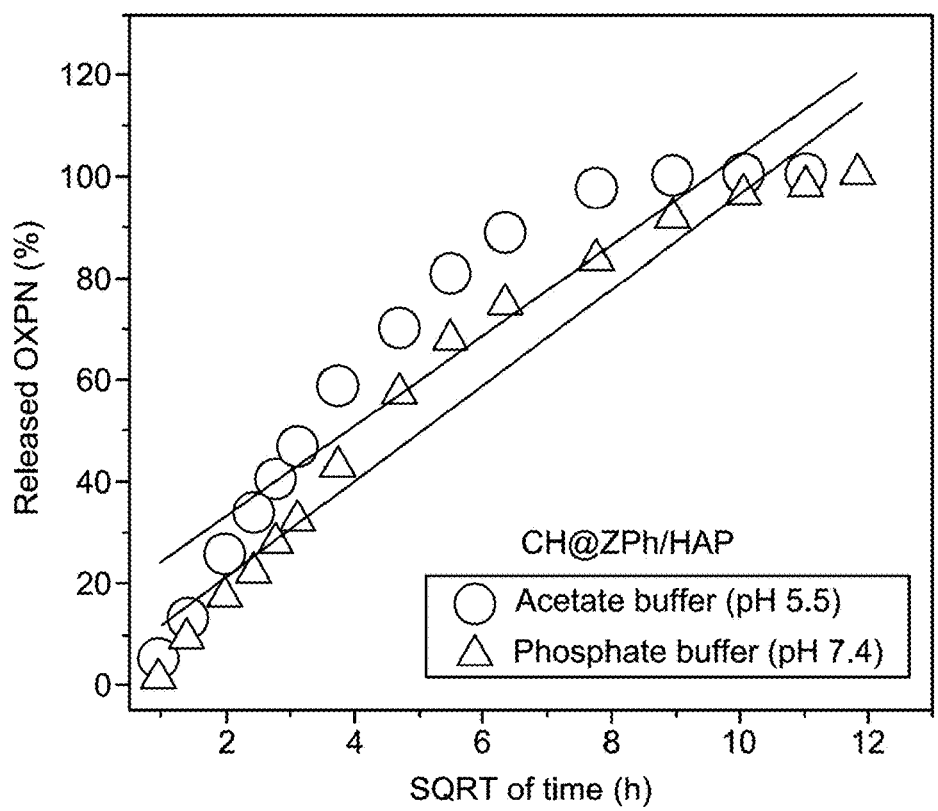
FIG. 11F illustrates the fitting of the OXPN release results with the Higuchi model CH@ZPh/HPA$_{NRs}$, according to certain embodiments.
Figure 11G:
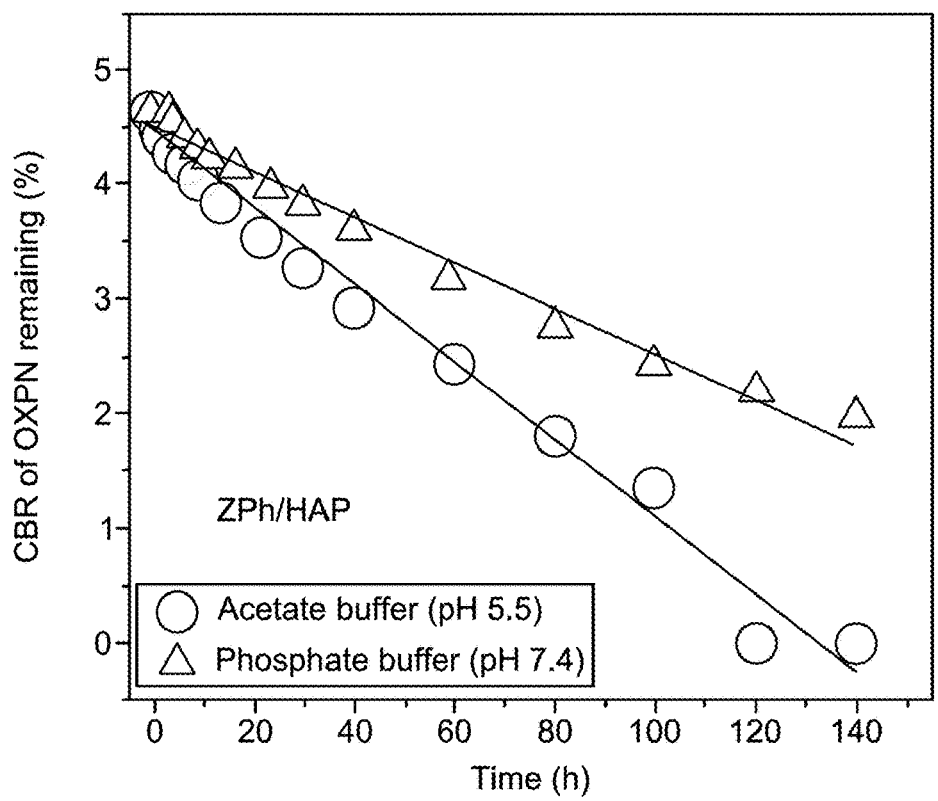
FIG. 11G illustrates the fitting of the OXPN release results with the Hixson-Crowell model ZPh/HPA$_{NRs}$, according to certain embodiments.
Figure 11H:
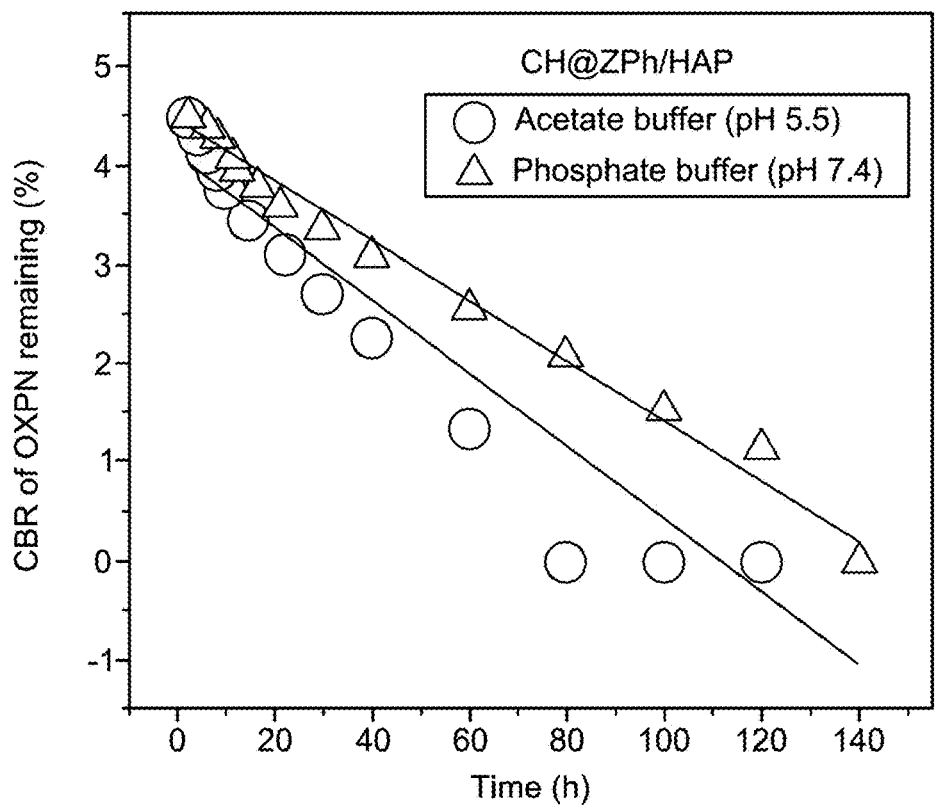
FIG. 11H illustrates the fitting of the OXPN release results with the Hixson-Crowell model CH@ZPh/HPA$_{NRs}$, according to certain embodiments.

The Korsmeyer-Peppas model can be applied to describe drug release from a polymer-based delivery system. The kinetic outcomes of the Korsmeyer-Peppas model indicate that coordinated diffusion and erosion mechanisms regulate drug-release reactions. FIGS. 9C-9D illustrate the first-order kinetics (Table 1) that were identified to describe the release kinetics of OXPN from ZPh/HPA$_{NRs}$ and FIGS. 11A-11B illustrates CH@ZPh/HPA$_{NRs}$ more perfectly than the zero-order kinetics (Table 1). FIGS. 11E-11F illustrates the loading drug dosages affected the release quantities of OXPN in all buffers tested. Excellent $R^2$ values can be observed during the fitting of the results with the Higuchi model (Table 1) and FIGS. 11G-11H illustrate the Hixson-Crowell model (Table 1). These results imply that collaboration between diffusion and erosion processes is the main factor affecting the release reactions of OXPN.

Figure 11I:
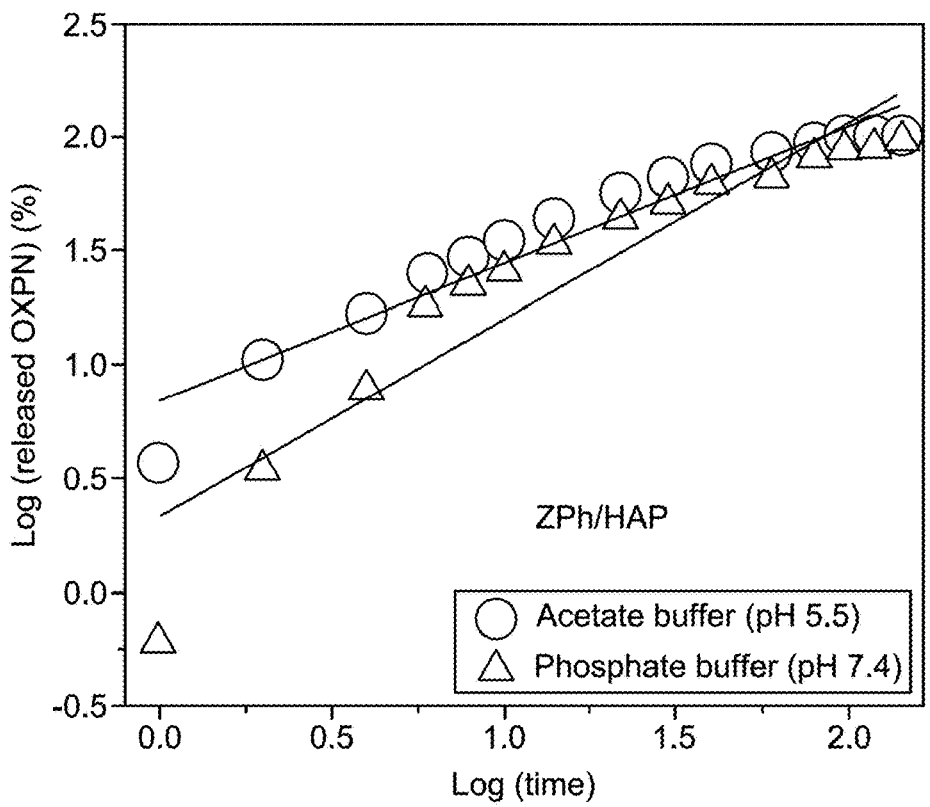
FIG. 11I illustrates the fitting of the OXPN release results with Korsmeyer-Peppas model ZPh/HPA$_{NRs}$, according to certain embodiments.
Figure 11J:
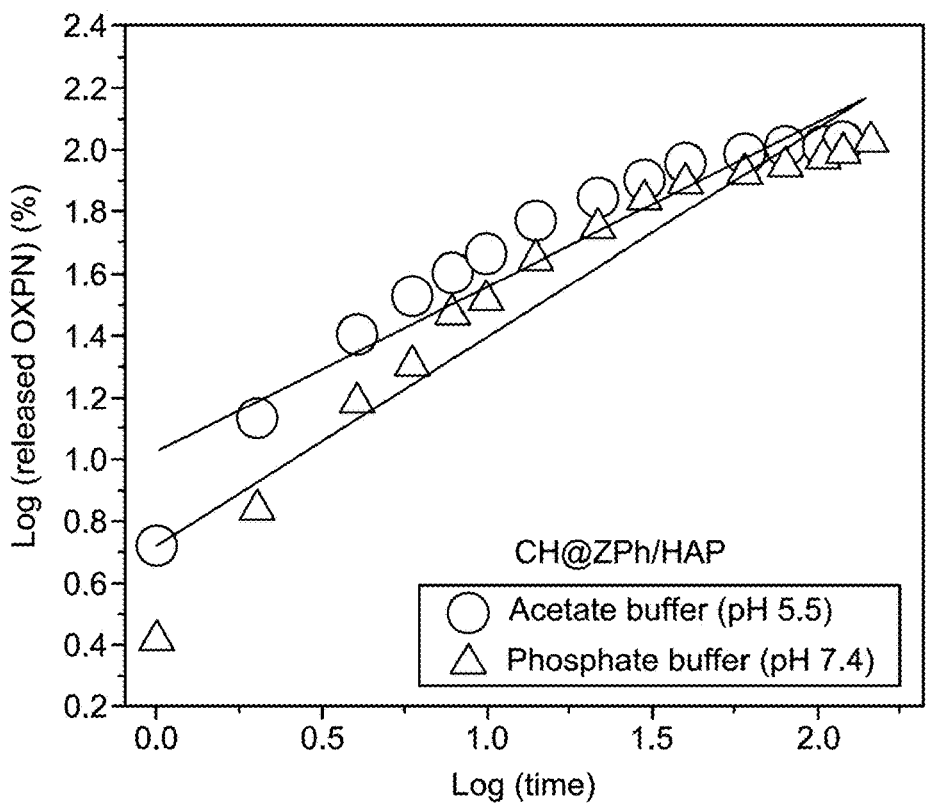
FIG. 11J illustrates the fitting of the OXPN release results with Korsmeyer-Peppas model CH@ZPh/HPA$_{NRs}$, according to certain embodiments.

FIG. 11I-11J illustrate the implementation of the Korsmeyer-Peppas model, which showed a degree of fit (Table 1) and confirms the successful operation of the cooperative erosion/diffusion release mechanisms. The numerical values of the diffusional exponent (n), according to Korsmeyer-Peppas modeling, can be used as evidence of the mechanisms that are influencing the release activities of OXPN. The OXPN showed n values <0.45 in pH 5.5 and pH 7.4 buffers, either by ZPh/HPA$_{NRs}$ or CH@ZPh/HPA$_{NRs}$, indicating the presence of non-Fickian transport release. Therefore, coordinated diffusion and erosion processes controlled the release mechanisms of OXPN.

Example 11: Cytotoxicity Properties

The cytotoxic effect of the free ZPh/HPA$_{NRs}$ and CH@ZPh/HPA$_{NRs}$ particles on normal colorectal fibroblast cells (CCD-18Co) was evaluated as an essential factor to assess the biocompatibility and safety value of the studied cancer on normal and non-infected cells. The cytotoxicity of free ZPh/HPA$_{NRs}$ and CH@ZPh/HPA$_{NRs}$ particles, as well as their OXPN-loaded products, was evaluated against the target human colorectal cancer cell (HCT-116) to determine its value as an anticancer agent and as a carrier of enhanced impact on the therapeutic effect of the loaded OXPN drug.

Regarding the cytotoxic effect of free ZPh/HPA$_{NRs}$ and CH@ZPh/HPA$_{NRs}$ particles on the CCD-18Co normal cells, the composite particles display high biocompatible and safe properties on the normal cell lines within the evaluated experimental range of the applied dosages (20 to 120 g/L). The measured cell viability percentages during the treatment of the CCD-18Co normal cells with the highest tested dosage of the free ZPh/HPA$_{NRs}$ and CH@ZPh/HPA$_{NRs}$ particles (120 μg/L) are 91.7% and 88.3%, respectively.

Figure 12A:
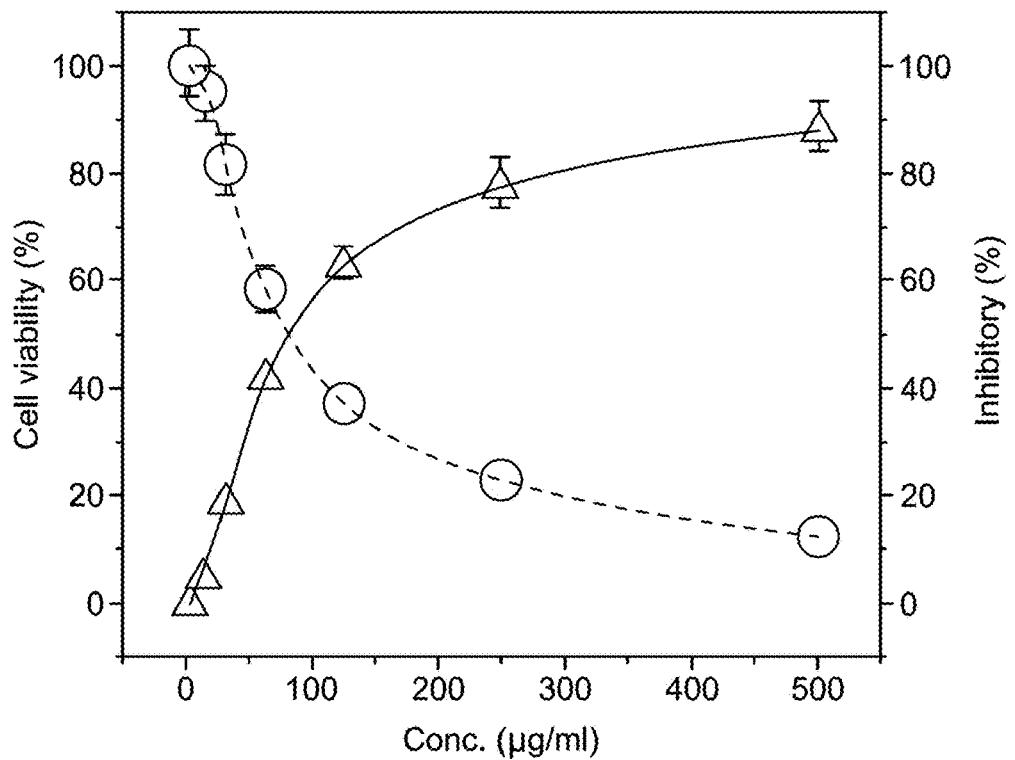
FIG. 12A illustrates the cytotoxicity effect of free ZPh/HPA$_{NRs}$ on colorectal cancer cell line (HCT-116), according to certain embodiments.
Figure 12B:
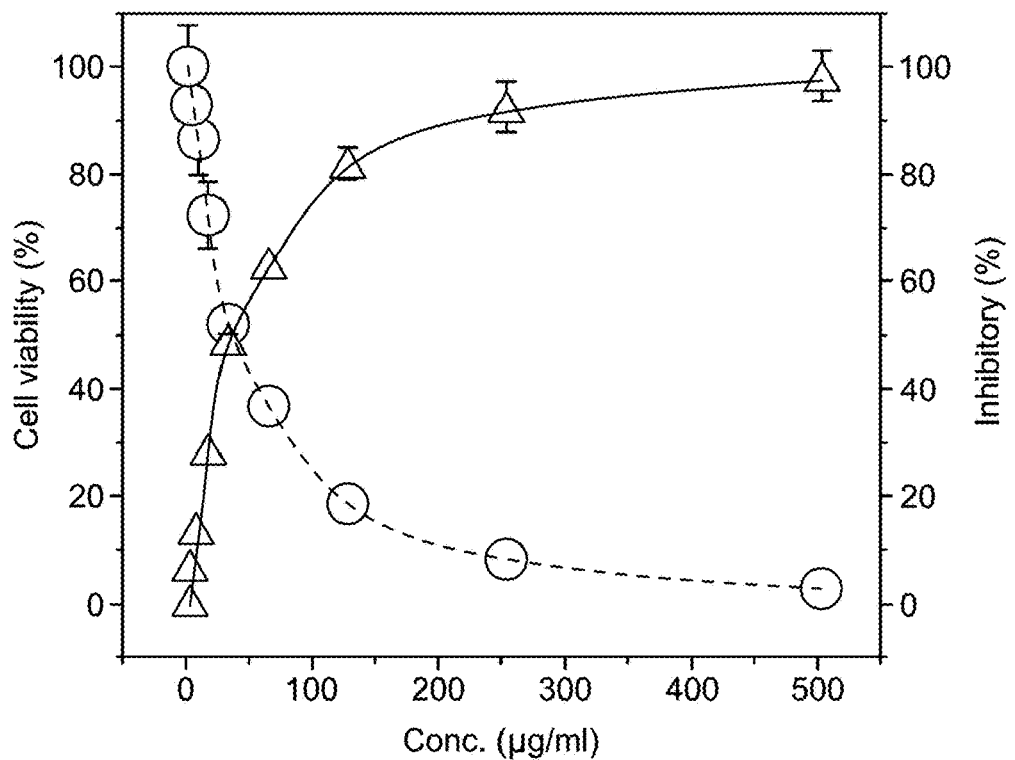
FIG. 12B illustrates the cytotoxicity effect of free CH@ZPh/HPA$_{NRs}$ on HCT-116, according to certain embodiments.

Regarding the cytotoxic impacts of the free ZPh/HPA$_{NRs}$ and CH@ZPh/HPA$_{NRs}$ particles on the infected HCT-116 cells, FIG. 12A illustrates the synthetic composite as free particles displaying considerable cytotoxicity against the tumor cells, especially at the applied dosages higher than 50 μg/mL. FIG. 12A illustrates the measured cell viability percentage, inhibitory percentage, and IC-50 value in the presence of 500 μg/mL of free ZPh/HPA$_{NRs}$ particles are 12.28%, 87.82%, and 91.9 μg/mL respectively, while FIG. 12B illustrates the reported values of free CH@ZPh/HPA$_{NRs}$ are 9.53% (cell viability), 90.47% (inhibitory percentage), and 86.9 g/mL (IC-50 value). Such cytotoxic results validate the promising biological activity of ZPh/HPA$_{NRs}$, which is enhanced at a considerable rate after its functionalization with chitosan (CH@ZPh/HPA$_{NRs}$).

Figure 12C:
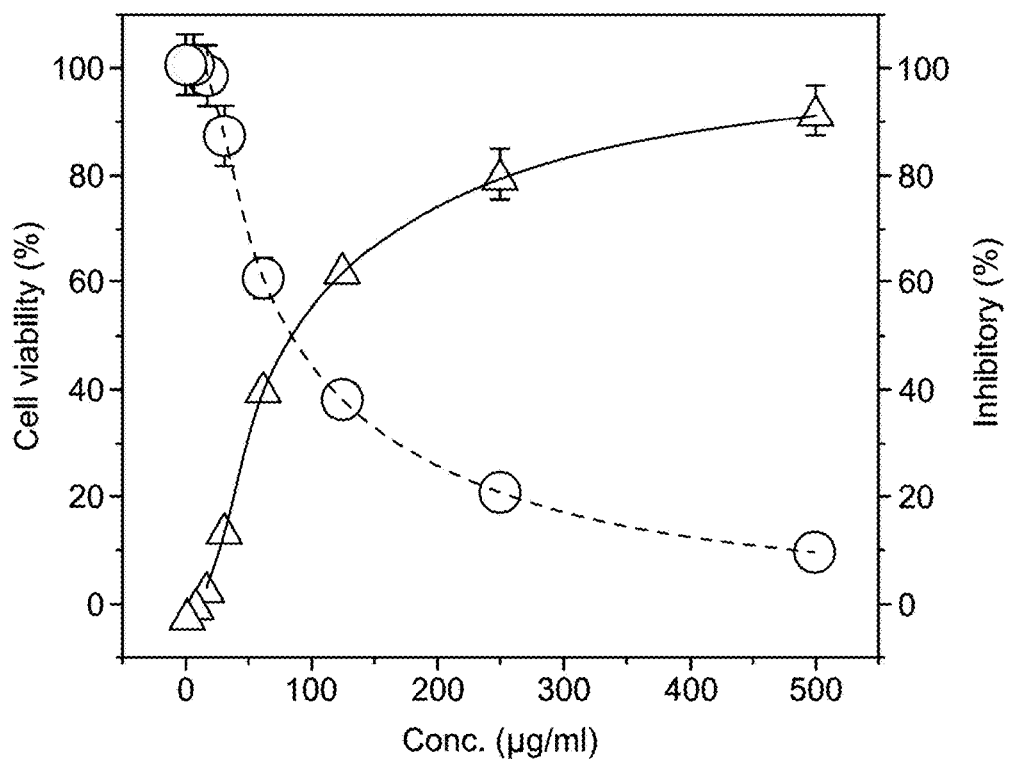
FIG. 12C illustrates the cytotoxicity effect of OXPN-loaded ZPh/HPA$_{NRs}$ on HCT-116, according to certain embodiments.
Figure 12D:
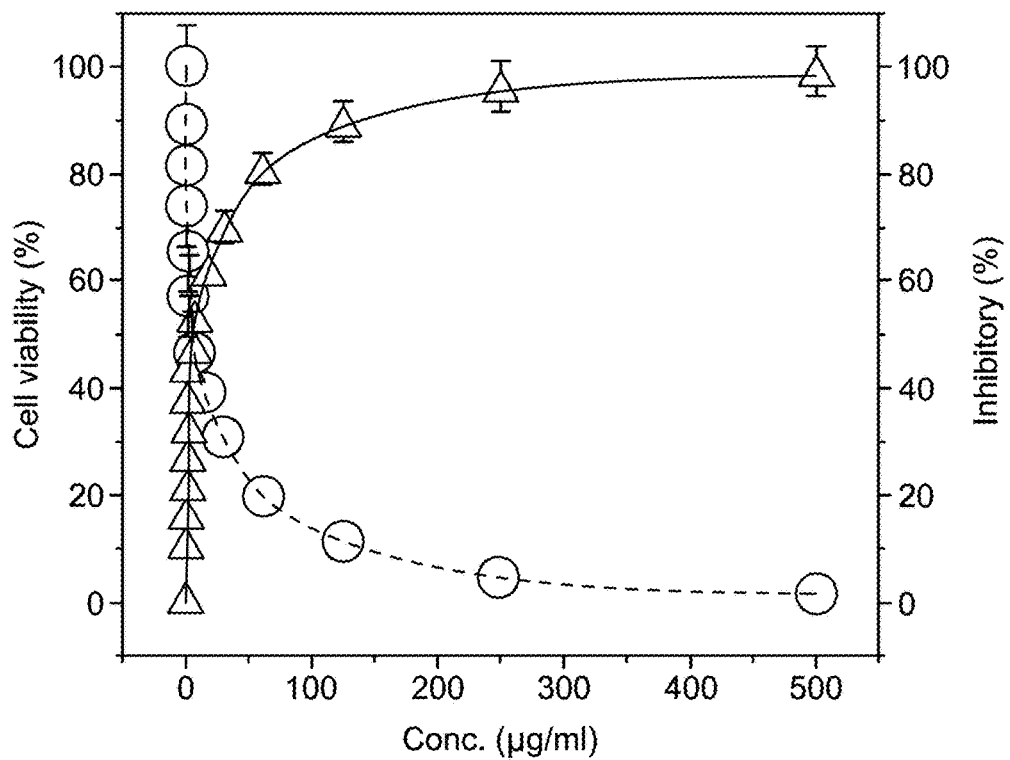
FIG. 12D illustrates the cytotoxicity effect of OXPN loaded CH@ZPh/HPA$_{NRs}$ on HCT-116, according to certain embodiments.

FIG. 12C illustrates the cytotoxicity properties of OXPN-encapsulated ZPh/HPA$_{NRs}$ against HCT-116 cancer cells; the application of the same dosage of the free particles (500 μg/mL) resulted in 2.91% cell viability percentage, 97.09% inhibitory percentage, and 35.34 μg/mL as IC-50. FIG. 12D illustrates the OXPN-loaded CH @ZPh/HPA$_{NRs}$; the determined values are 1.83% as cell viability percentage, 98.17% as inhibitory percentage, and 6.79 μg/mL as IC-50. Such cytotoxic results demonstrate the enhancement impact of the used ZPh/HPA$_{NRs}$ and CH@ZPh/HPA$_{NRs}$ carriers on the cytotoxic effects and the therapeutic impact of the loaded OXPN drug as common chemotherapy in addition to its previously determined controlling effects on the loading and release behaviors.

TABLE 2 compares the loading capacities and release periods of the studied carrier with those of other carriers in the literature.

| Carrier | Loading capacity (mg/g) | Release period pH 5.5 | Release period pH 7.4 | References |
| --- | --- | --- | --- | --- |
| Hydroxyapatite | 49.1 | | | M. Betsiou et. al., Ceram. Int. 38 (4) (2012) 2719-2724. |
| Cellulose/zeolite-A | 285.7 | 110 h | 150 h | N. Altoom, et. al., J. Sol-Gel Sci. Technol. 103 (3) (2022) 752-765. |
| Zeolite-A | 109.03 | 150 h | 150 h | N. Altoom, et. al., J. Sol-Gel Sci. Technol. 103 (3) (2022) 752-765. |
| β-Cyclodextrin/ phillipsite | 291.5 | 140 h | 180 h | N. Altoom, et. al., Colloids Surf. A Physicochem. Eng. Asp. 648 (2022), 129144. |
| Phillipsite | 79.6 | 180 h | 180 h | N. Altoom, et. al., Colloids Surf. A Physicochem. Eng. Asp. 648 (2022), 129144. |
| β-Cyclodextrin/ diatomite | 238.7 | 80 h | 120 h | H.E. Alfassam, et. al., Int. J. Biol. Macromol. 235 (2023), 123825. |
| Diatomite | 65.9 | 160 h | 200 h | H.E. Alfassam, et. al., J. Macromolec. Sci. B (2023) |
| ZPh/HPA$_{NRs}$ | 127.2 | 120 h | 140 h | This study |
| CH@ZPh/HPA$_{NRs}$ | 321.75 | 80 h | 140 h | This study |

The OXPN loading capacities of ZPh/HPA$_{NRs}$ and CH@ZPh/HPA$_{NRs}$ at their saturation states were compared with the reported capacities of other investigated materials and structures in the literature (Table 2). The presented loading capacities validate the higher properties of both ZPh/HPA$_{NRs}$ and CH@ZPh/HPA$_{NRs}$ as compared to synthetic hydroxyapatite, zeolite (zeolite-A), natural zeolite (philipsite), diatomite, kaolinite, and their based composites.

Numerous modifications and variations of the present disclosure are possible in light of the above teachings. It is, therefore, to be understood that within the scope of the appended claims, the invention may be practiced otherwise than as specifically described herein.

The invention claimed is:
1. A drug delivery system, comprising a nanocomposite, wherein the nanocomposite comprises:
   a zinc phosphate core;
   a hydroxyapatite shell; and
   chitosan;
   wherein the hydroxyapatite shell at least completely encloses the zinc phosphate core,
   wherein the chitosan at least partially wraps around the hydroxyapatite shell, wherein the chitosan interacts with the hydroxyapatite shell through hydrogen bonding, and
wherein the nanocomposite is loaded with oxaliplatin to form the drug delivery system.

2. The drug delivery system of claim 1, wherein the hydroxyapatite shell is in a form of nanorods.

3. The drug delivery system of claim 2, wherein the nanorods have an average length in a range of from 1 to 10 µm.

4. The drug delivery system of claim 3, wherein the nanorods have an average width in a range of 5 to 400 µm, and
wherein the nanorods are oriented tangentially to a surface of the zinc phosphate core.

5. The drug delivery system of claim 1, wherein a hydroxyapatite in the hydroxyapatite shell has an average crystallite size in a range of 6 to 8 nm.

6. The drug delivery system of claim 1, wherein a zinc phosphate in the zinc phosphate core has an average crystallite size in a range of 7 to 9 nm.

7. The drug delivery system of claim 1, wherein the zinc phosphate core and the hydroxyapatite shell are separate crystalline phases.

8. The drug delivery system of claim 1, wherein the zinc phosphate core is porous and comprises nanopores and micropores.

9. The drug delivery system of claim 1, wherein the zinc phosphate core is spherical and has an average diameter in a range of 10 to 100 µm.

10. The drug delivery system of claim 1, wherein the nanocomposite has a BET surface area in a range of 120-140 $m^2/g$.

11. The drug delivery system of claim 1, wherein the nanocomposite has an average pore diameter in a range of 25-35 nm.

12. The drug delivery system of claim 1, wherein the nanocomposite comprises O, N, P, Ca, Mg, and Zn.

13. The drug delivery system of claim 1, comprising the oxaliplatin in a range of from 300 to 350 mg per gram of the nanocomposite, when loading conditions have a pH in a range of from 6 to 8, a temperature in a range of from 20 to 30° C. and takes place for at least 6 hours.

14. The drug delivery system of claim 1, wherein the oxaliplatin interacts with the zinc phosphate core, the hydroxyapatite shell and/or the chitosan through at least one of Van der Waals forces, hydrogen bonding, electrostatic interactions, chemical complexes, and ion exchange.

15. The drug delivery system of claim 1, wherein a portion of the oxaliplatin is entrapped in pores of the nanocomposite.

16. The drug delivery system of claim 1, wherein the oxaliplatin, the zinc phosphate core, the hydroxyapatite shell and the chitosan do not interact through covalent bonds.

17. The drug delivery system of claim 1, having a release percentage of the oxaliplatin of at least 50% after 22 hours in an environment having a pH of 7.4.

18. The drug delivery system of claim 1, having a release percentage of the oxaliplatin of 100% after 140 hours in an environment having a pH of 7.4.

19. The drug delivery system of claim 1, comprising the oxaliplatin in a range of from 300 to 350 mg per gram of the nanocomposite.

20. The drug delivery system of claim 1, wherein the zinc phosphate core is spherical and has an average diameter in a range of from 10 to 100 µm,
wherein the nanocomposite has a BET surface area in a range of from 120 to 140 m2/g, and
wherein the nanocomposite has an average pore diameter in a range of from 25 to 35 nm.

* * * * *